(12) United States Patent
King et al.

(10) Patent No.: US 12,369,604 B2
(45) Date of Patent: Jul. 29, 2025

(54) METHODS OF INHIBITION WITH MICROBIAL STRAINS AND ANTIBIOTICS

(71) Applicant: MICROBIAL DISCOVERY GROUP, LLC, Franklin, WI (US)

(72) Inventors: Michael R. King, Oak Creek, WI (US); Sona Son, Cudahy, WI (US); Kyle Leistikow, Cudahy, WI (US)

(73) Assignee: MICROBIAL DISCOVERY GROUP, LLC, Franklin, WI (US)

( * ) Notice: Subject to any disclaimer, the term of this patent is extended or adjusted under 35 U.S.C. 154(b) by 652 days.

(21) Appl. No.: 17/637,013

(22) PCT Filed: Aug. 21, 2020

(86) PCT No.: PCT/US2020/047390
§ 371 (c)(1),
(2) Date: Feb. 21, 2022

(87) PCT Pub. No.: WO2021/035137
PCT Pub. Date: Feb. 25, 2021

(65) Prior Publication Data
US 2022/0295828 A1 Sep. 22, 2022

Related U.S. Application Data

(60) Provisional application No. 62/890,267, filed on Aug. 22, 2019.

(51) Int. Cl.
| | | |
|---|---|---|
| *A23K 10/18* | (2016.01) | |
| *A23K 20/189* | (2016.01) | |
| *A61K 35/742* | (2015.01) | |
| *A61P 31/04* | (2006.01) | |

(52) U.S. Cl.
CPC ............ *A23K 10/18* (2016.05); *A23K 20/189* (2016.05); *A61K 35/742* (2013.01); *A61P 31/04* (2018.01)

(58) Field of Classification Search
CPC ...... A23K 10/18; A23K 20/189; A23K 50/10; A23K 50/20; A23K 50/80; A23K 50/40; A23K 50/30; A23K 50/60; A23K 50/75; A61K 35/742; A61K 2035/115; A61P 31/04; C12R 2001/07; C12N 1/20; C12N 1/205
See application file for complete search history.

(56) References Cited

U.S. PATENT DOCUMENTS

| | | | |
|---|---|---|---|
| 4,673,638 A | 6/1987 | Grosch et al. | |
| 5,587,475 A | 12/1996 | Helquist et al. | |
| 5,589,381 A | 12/1996 | Neyra et al. | |
| 5,665,354 A | 9/1997 | Neyra et al. | |
| 6,268,147 B1 | 7/2001 | Beattie et al. | |
| 7,754,469 B2 | 7/2010 | Baltzley et al. | |
| 7,807,185 B2 | 10/2010 | Farmer | |
| 8,025,874 B2 | 9/2011 | Bellot et al. | |
| 8,540,981 B1 | 9/2013 | Wehnes et al. | |
| 9,175,258 B2 | 11/2015 | Bywater-Ekegard et al. | |
| 9,410,213 B2 | 8/2016 | Matheny et al. | |
| 9,758,414 B2 | 9/2017 | Dash et al. | |
| 9,844,573 B2 | 12/2017 | Nielsen et al. | |
| 10,335,440 B2 * | 7/2019 | King | A61K 38/43 |
| 10,357,046 B2 * | 7/2019 | King | A23K 10/18 |
| 10,905,135 B2 * | 2/2021 | King | A23K 50/10 |
| 10,961,275 B2 | 3/2021 | Bralkowski et al. | |
| 11,110,134 B2 * | 9/2021 | King | A23K 20/195 |
| 11,944,656 B2 * | 4/2024 | King | A23K 20/189 |
| 11,998,576 B2 * | 6/2024 | King | A61K 38/43 |
| 2001/0027947 A1 | 10/2001 | Tsuchiya | |
| 2004/0247582 A1 | 12/2004 | Binder et al. | |
| 2005/0255092 A1 | 11/2005 | Rehberger et al. | |
| 2005/0266468 A1 | 12/2005 | Bedzyk et al. | |
| 2005/0271643 A1 | 12/2005 | Sorokulova et al. | |
| 2006/0188978 A1 | 8/2006 | Grant | |
| 2008/0050774 A1 | 2/2008 | Berka et al. | |
| 2009/0238907 A1 | 9/2009 | Farmer | |
| 2009/0280090 A1 | 11/2009 | Rehberger et al. | |
| 2010/0010080 A1 | 1/2010 | Mockett et al. | |
| 2010/0062021 A1 | 3/2010 | Winkelman | |
| 2010/0092428 A1 | 4/2010 | Schmidt et al. | |
| 2010/0291564 A1 | 11/2010 | Stanley et al. | |
| 2012/0100118 A1 | 4/2012 | Rehberger et al. | |
| 2012/0177620 A1 | 7/2012 | Farmer | |
| 2012/0315258 A1 | 12/2012 | Rehberger et al. | |
| 2012/0315259 A1 | 12/2012 | Friedlander | |
| 2013/0064927 A1 | 3/2013 | Davis et al. | |

(Continued)

FOREIGN PATENT DOCUMENTS

| | | |
|---|---|---|
| CA | 2869036 A1 | 10/2013 |
| CA | 2948832 A1 | 11/2015 |

(Continued)

OTHER PUBLICATIONS

Paradis et al. (BMC Med Genet, 2010, 11:54) (Year: 2010).
PCT Search Report and Written Opinion for PCT/US2015/030578, completed Jul. 9, 2015.
PCT Search Report and Written Opinion for PCT/US2016/030223, completed Jul. 29, 2016.
PCT Search Report and Written Opinion prepared for PCT/US2020/023586, Jun. 19, 2020.
Peng, et al., "Evaluation of antiviral activity of Bacillus licheniformis-fermented products against porcine epidemic diarrhea virus," AMB Express, Dec. 3, 2019, 9(191): 1-12.
Rajendram et al., Journal of Microbiological Methods, 2006, 67, 582-92.
Ramachandran et al., "A Broad-Spectrum Antimicrobial Activity of Bacillus subtilis RLID 12.1," 2014.

(Continued)

*Primary Examiner* — Robert B Mondesi
*Assistant Examiner* — Alexander B Pastora
(74) *Attorney, Agent, or Firm* — Barnes & Thornburg LLP

(57) ABSTRACT

The invention relates to direct-fed microbials for use in *E. coli* and/or *Clostridium* inhibition in animals in combination with antibiotics. More particularly, the invention relates to isolated *Bacillus* strains 2, 3, 4, 5, 6, 7, 9, 57, 71, and 126, and strains having all of the identifying characteristics of these strains, for a use comprising the above-mentioned use.

22 Claims, 13 Drawing Sheets

(56) References Cited

U.S. PATENT DOCUMENTS

| | | | |
|---|---|---|---|
| 2013/0098837 A1 | 4/2013 | Dash et al. |
| 2013/0100118 A1 | 4/2013 | Mlyniec et al. |
| 2013/0136695 A1 | 5/2013 | Hargis et al. |
| 2013/0216586 A1 | 8/2013 | LeBrun et al. |
| 2013/0295067 A1 | 11/2013 | Baltzley et al. |
| 2014/0106974 A1 | 4/2014 | Sun et al. |
| 2014/0141044 A1 | 5/2014 | Bhatt et al. |
| 2014/0273150 A1 | 9/2014 | Angel |
| 2014/0315716 A1 | 10/2014 | Matheny et al. |
| 2014/0363819 A1 | 12/2014 | Rowlyk et al. |
| 2015/0079058 A1 | 3/2015 | Nielsen et al. |
| 2015/0111214 A1 | 4/2015 | Liu |
| 2015/0147303 A1 | 5/2015 | Hsieh |
| 2015/0216203 A1 | 8/2015 | Isaksen et al. |
| 2015/0216916 A1 | 8/2015 | Galbraith et al. |
| 2015/0250832 A1 | 9/2015 | De Brueker et al. |
| 2015/0250842 A1 | 9/2015 | Calabotta et al. |
| 2016/0108467 A1 | 4/2016 | Semikhodskii et al. |
| 2017/0079308 A1 | 3/2017 | King et al. |
| 2017/0106027 A1 | 4/2017 | Tonda et al. |
| 2017/0166466 A1 | 6/2017 | King et al. |
| 2017/0246224 A1* | 8/2017 | King .................... A61K 45/06 |
| 2017/0327840 A1 | 11/2017 | Kijlstra et al. |
| 2018/0170968 A1 | 6/2018 | Bralkowski et al. |
| 2018/0361444 A1 | 12/2018 | Franssen et al. |
| 2019/0021341 A1 | 1/2019 | Davis et al. |
| 2019/0201458 A1 | 7/2019 | Frouel et al. |
| 2020/0015497 A1 | 1/2020 | King et al. |
| 2020/0029592 A1 | 1/2020 | King et al. |
| 2020/0093158 A1 | 3/2020 | Calabotta et al. |
| 2020/0281225 A1 | 9/2020 | Kiarie et al. |
| 2020/0359653 A1 | 11/2020 | Johnson et al. |
| 2021/0112815 A1 | 4/2021 | McBride et al. |
| 2021/0154242 A1 | 5/2021 | Keller et al. |
| 2022/0143110 A1 | 5/2022 | Lewis et al. |

FOREIGN PATENT DOCUMENTS

| | | | |
|---|---|---|---|
| CN | 101076585 A | 11/2007 |
| CN | 101159102 A | 4/2008 |
| CN | 101405411 A | 4/2009 |
| CN | 101926830 A | 12/2010 |
| CN | 102223809 A | 10/2011 |
| CN | 102885202 A | 1/2013 |
| CN | 103980535 A | 8/2014 |
| CN | 104411182 A | 3/2015 |
| CN | 104735999 A | 6/2015 |
| CN | 106265880 A | 1/2017 |
| CN | 106420841 A | 2/2017 |
| CN | 106714570 A | 5/2017 |
| CN | 107841478 A | 3/2018 |
| CN | 108208315 A | 6/2018 |
| CN | 109497281 A | 3/2019 |
| CN | 109561712 A | 4/2019 |
| CN | 110573606 A | 12/2019 |
| CN | 113286510 A | 8/2021 |
| EP | 1574564 A1 | 9/2005 |
| GB | 1392813 A | 4/1975 |
| GB | 1434582 A | 5/1976 |
| JP | 2001169760 A | 6/2001 |
| JP | 3417904 B2 | 6/2003 |
| KR | 100427600 B1 | 4/2004 |
| WO | 2005019417 A2 | 3/2005 |
| WO | 2007083147 A2 | 7/2007 |
| WO | 2010/032233 A2 | 3/2010 |
| WO | 20100033714 A1 | 3/2010 |
| WO | 2012/009712 A2 | 1/2012 |
| WO | 2012101528 A2 | 8/2012 |
| WO | 2014020141 A1 | 2/2014 |
| WO | 2014067081 A1 | 5/2014 |
| WO | 20140172520 A1 | 10/2014 |
| WO | 2015057330 A1 | 4/2015 |
| WO | 2015132085 A1 | 9/2015 |
| WO | 2015160960 A1 | 10/2015 |
| WO | WO-2015175667 A1 * | 11/2015 | .............. A23K 10/16 |
| WO | 2017081105 A1 | 5/2017 |
| WO | 2017151608 A1 | 9/2017 |
| WO | 2017/205645 A1 | 11/2017 |
| WO | 2018148847 A1 | 8/2018 |
| WO | 2018/167171 A1 | 9/2018 |
| WO | 2019090068 A1 | 5/2019 |
| WO | 2019090088 A1 | 5/2019 |
| WO | 2019141815 A1 | 7/2019 |
| WO | 2019/152791 A1 | 8/2019 |
| WO | 2019/213243 A1 | 11/2019 |
| WO | 2020069255 A1 | 4/2020 |
| WO | 2020072578 A1 | 4/2020 |
| WO | 2021035137 A1 | 2/2021 |
| WO | 2021041603 A1 | 3/2021 |
| WO | 2023018686 A1 | 2/2023 |

OTHER PUBLICATIONS

Safitri et al. "Ability of Bacterial Consortium: *Bacillus coagulans*, *Bacilus licheniformis*, *Bacillus pumilus*, *Bacillus subtilis*, *Nitrosomonas* sp. and *Pseudomonas putida* in Bioremediation of Waste Water in; Cisirung Waste Water Treatment Plant," Agrolife Scientific Journal, 2015, vol. 4, No. 1, pp. 146-152.

Schmidt et al., "New Concepts of microbial treatment processes for the nitrogen removal in wastewater," 2003.

Search Report for copending CN Application No. 202080037387.1, mailed Dec. 3, 2023.

Sheldon et al. (2009). Defining postpartum uterine disease and the mechanisms of infection and immunity in the female reproductive tract in cattle. Biol Reprod 81:1025-1032.

Sonune et al., "Isolation, characterization and identification of extracellular enzyme producer Bacillus licheniformis from municipal wastewater and evaluation of the biodegradability," Biotechnology Research and Innovation, Jan.-Dec. 2018, vol. 2, No. 1, pp. 37-44.

Souza et al. J. Anim. Sci. vol. 90, Suppl. 3/J. Dairy Sci. vol. 95, Suppl. 2 T281.

Sumi et al, Antimicrobial peptides of the genus *Bacillus*: a new era for antibiotics, Nov. 19, 2014, p. 1-7.

Supp. European Search Report, European Application No. 20858946, dated Aug. 23, 2023.

Wampfler et al. (Pl-os one, 2013, p. 1-12) (Year: 2013).

West et al. (2007) Rapid Detection of *Escherichia coli* Virulence Factor Genes using Multiplex Real-Time TaqMan® PCR Assays. Veterinary Microbiology 122(3-4): 323-331.

White et al. (Infection and Immunity, 2014, 82(4):1559-1571) (Year: 2014).

Yatsuyanagi et al. (2002). Characterization of enteropathogenic and enteroaggregative *Escherichia coli* isolated from diarrheal outbreaks, Journal of Clinical Microbiology, vol. 40, No. 1, pp. 294-297.

Zganjer et al. Treatment of rectal prolapse in children with cow milk injection sclerotherapy: 30-year experience, World Journal of Gastroanterology, 2008, 14(5) 740-7.

C. Zuckermann, Federico A et al. "Bacillus-Based Direct-Fed Microbial Reduces the Pathogenic Synergy of a Coinfection with *Salmonella enterica* Serovar Choleraesuis and Porcine Reproductive and Respiratory Syndrome Virus." Infection and immunity vol. 90,4 (2022): e0057421. doi: 10.1128/iai.00574-21.

Abdelwhab et al., "The use of FTA® filter papers for diagnosis of avian influenza virus". J. Virological Meth., 174:120-122, Mar. 17, 2011 (Mar. 17, 2011).

Abutarbush et al. (2004). Jejunal hemorrhage syndrome in 2 Canadian beef cows. Can. Vet. J. 45, 48-50.

Abutarbush et al. (2005). Jejunal hemorrhage syndrome in dairy and beef cattle: 11 cases (2001 to 2003). Can. Vet. J. Rev. Vét. Can. 46, 711-715.

Adaska et al. (2014). Jejunal hematoma in cattle: a retrospective case analysis. J. Vet. Diagn. Investig. Off. Publ. Am. Assoc. Vet. Lab. Diagn. Inc 26, 96-103.

Albini et al. (2010). Real-time multiplex PCR assays for reliable detection of Clostridium perfringens toxin genes in animal isolates, Veterinary Microbiology, 127 (1-2): 179-185.

(56) References Cited

OTHER PUBLICATIONS

Bae H.D., Yanke L.J, Cheng K.J., Selinger L.B., 1999, "A novel staining method for detecting phytase activity," Journal of Microbiological Methods, 39:1, 17-22.
Baines et al. (2011). Mouldy feed, mycotoxins and Shiga toxin-producing Escherichia coli colonization associated with Jejunal Hemorrhage Syndrome in beef cattle. BMC Vet. Res. 7, 24.
Bankamp et al., "Improving molecular tools for global surveillance of measles virus". J. Clin. Virology, 58 Sep. 2013, (Sep. 2013).
Byoung-Joo et al. (Acta Vet Beograd, 2017, 67: 153) (Year: 2017).
Canning, et al., "Effect of direct-fed microbial Bacillus subtilis C-3102 on enteric health in nursery pigs after challenge with porcine epidemic diarrhea virus," Journal of Swine Health and Production, May 3, 2017, 25(3): 129-137.
Ceci, L., Paradies, P., Sasanelli, M., De Caprariis, D., Guarda, F., Capucchio, M. t., and Carelli, G. (2006). Haemorrhagic Bowel Syndrome in Dairy Cattle: Possible Role of Clostridium perfringens Type A in the Disease Complex. J. Vet. Med. Ser. A 53, 518-523.
Chen et al, 2013 J of Proteone Research, 12, p. 1151-1161.
Choudhary et al. 2009 (Interactions of Bacillus spp. and plants—with special reference to induced systemic resistance (ISR); Microbiological Research 164: 493-513). (Year:2009).
Cohn et al "Bacillus strains improving health and performance of production animals" ip.com Feb. 11, 2016.
Cranford E. Good Nutrition Vital for Pregnant Cows. NDSU. 2016; 1.
Credille et al. (2014). Prevalence of bacteremia in dairy cattle with acute puerperal metritis. J Vet Intern Med, 28:1606-1612.
De Crignis et al. (J of Virol Methods, 2010, 165, 51-56) (Year: 2010).
Dennison et al. (2002). Hemorrhagic bowel syndrome in dairy cattle: 22 cases (1997-2000). J. Am. Vet. Med. Assoc. 221, 686-689.
Dennison et al. (2005). Comparison of the odds of isolation, genotypes, and in vivo production of major toxins by Clostridium perfringens obtained from the gastrointestinal tract of dairy cows with hemorrhagic bowel syndrome or left-displaced abomasum. J. Am. Vet. Med. Assoc. 227, 132-138.
Dobbs et al , 2002 Arch Pathol Lab Med. vol. 126, p. 56-63.
EP search report in EP 16789853 completed Aug. 8, 2018.
EPA, Final Risk assessment of Bacillus Subtilis, Feb. 1997, p. 3, 9 (1997).
European Search Report, European Application No. 20855232.3-1105 dated Aug. 31, 2023, 8 pages.
Extended European Search Report, European Application No. 15792802.9-1358 dated Nov. 8, 2017, 8 pages.
Fei et al., "A laboratory landfill simulator for physical, geotechnical, chemical and microbial characterization of solid waste biodegradation processes," Couples Phenomena in Environmental Geotechnics, May 20, 2013 (May 20, 2013), Taylor & Francis Group, London, pp. 321-327.
Frydendahl et al. (2001). Automated 5' nuclease assay for detection of virulence factors in porcine Escherichia coli. Molec.Cell. Probes. 15: 151-160.
Haldar et al., "Development of a haemolysin gene-based multiplex PCR for simultaneous detection of Vibrio campbellii, Vibrio harveyi and Vibrio parahaemolyticus", Letters in Applied Microbiology 50 (2010) 146-152. Epub Nov. 5, 2009.
Harnentis et al. "Isolation, Characterization and Production of Mannanase from Thermophilic Bacteria to Increase the Feed Quality," Pakistan Journal of Nutrition 12 (4): 360-364, 2013.
International search report and written opinion for PCT/US2017/019941, mailed May 26, 2017.
International search report and written opinion for PCT/US2018/058948, mailed Jan. 18, 2019.
International search report and written opinion for PCT/US2019/030182, mailed Aug. 8, 2019.
International search report and written opinion for PCT/US2019/054190, mailed Feb. 10, 2020.
International Search Report prepared for PCT/US2020/047390, mailed Jan. 21, 2021.
International Search Report prepared for PCT/US2020/048101 mailed Jan. 22, 2021.
Jinneman et al. (2003). Multiplex Real-Time PCR Method To Identify Shiga Toxin Genes stx1 and stx2 and Escherichia coli 0157:H7/H—Serotype. Appl. Environ. Microbiol. Oct. 2003 vol. 69 No. 10 6327-6333.
Johnson et al. (2012). A MIQE—Compliant Real-Time PCR Assay for Aspergillus Detection., PLOSone., 7(7): 1-8.
Karigar et al., "Role of Microbial Enzymes in the Bioremediation of Pollutants: A Review," Enzyme Research, vol. 2011, Article ID 805187, 11 pages.
Kiarie et al. "The Role of Added Feed Enzymes in Promoting Gut Health in Swine and Poultry," Nutrition Research Reviews, Jun. 1, 2013 (Jun. 1, 2013), vol. 26, pp. 71-88. Entire document.
Krishnani, Genbank entry KJ000877 published Feb. 2014.
La Ragione et al. "Bacillus subtilis Spores Competitively Exclude Escherichia coli O78: K80 in Poultry," Veterinary Microbiology, Mar. 20, 2001 (Mar. 20, 2001). vol. 79, pp. 133-142. Entire document.
Lima et al. (Exp Parasitology, 2012, 132:348-354) (Year: 2012).
Lowe, et al., Nucleic Acids Research, 1990, 18(7) 1757-61.
Mahar et al., "Modeling and simulation of landfill gas production from pretreated MSW landfill simulator," Frontiers of Environmental Science & Engineering, Apr. 15, 2014 (Apr. 15, 2014), vol. 10, Iss. 1, pp. 159-167.
Malinen et al. (2003). Comparison of real-time PCR with SYBR Green I or 5 '-nuclease assays and dot-blot hybridization with rDNA-targeted oligonucleotide probes in quantification of selected faecal bacteria. Microbiology. 149:269-277.
Mapleton. About our Cows—Producing Milk & Pregnancy. Mapleton's Organic. 2016;1-3.
McClure et al. "Assessment of DNA extracted from FTA® cards for use on the Illumina iSelect Beach Chip," BMC Research Notes, 2009, 2(107) 4 pages.
Miller et al., "Sanitary Landfill Simulation: Test Parameters and a Simulator Conceptual Design," Naval Facilities Engineering Command: Civil Engineering Laboratory, Oct. 20, 1976 (Oct. 20, 1976), pp. 1-47. Retrieved from the Internet: <https://apps.dtic.mil/dtic/tr/fulltext/u2/a030998.pdf>.
Naslund et al. (J. of Virol Methods, 2011, 178: 186-190) (Year: 2011).
Nielsen et al. (2003). Detection and characterization of verocytotoxin-producing Escherichia coli by automated 5 nuclease PCR assay, Journal of ClinicalMicrobiology, vol. 41, No. 7, pp. 2884-2893.
Ou et al., "Identification of HIV-1 infected infants and young children using real-time RT PCR and dried blood spots from Uganda and Cameroon," Journal of Virological Methods, 2007, 144, 109-14.
PCT Search Report and Written Opinion prepared for PCT Application No. PCT/US2020/047390, completed Dec. 12, 2020.
Extended European Search Report for EP Application No. 21859032.1, mailed Jul. 30, 2024.
Extended European Search Report for EP Application No. 21859033.9, mailed Sep. 13, 2024.
International Search Report and Written Opinion for Application No. PCT/US23/76159, mailed Apr. 11, 2024.
Office Action and Search Report for copending Chinese Patent Application No. 202180069381.7, issued on Apr. 7, 2024.
PCT Search Report and Written Opinion prepared for PCT Application No. PCT/US2021/046451, completed Oct. 27, 2021.
PCT Search Report and Written Opinion prepared for PCT Application No. PCT/US2021/046452, completed Oct. 28, 2021.
Schmid, PJ et al. "Bacillus cereus in Packaging Material: Molecular and Phenotypical Diversity Revealed" pp. 1-11. Frontiers in Microbiology. vol. 12. Jul. 12, 2021; abstract; DOI: 10.3389/fmicb.2021.698974.
Trotter, "Bacillus Subtillis De111 Intake May Improve Blood Lipids and Endothelial Function in Healthy Adults" pp. 621-630. Beneficial Microbes. vol. 11, No. 7. Nov. 15, 2020; p. 623, p. 626; DOI: 10.3920/BM2020.0039.

* cited by examiner

| Pattern | Range |
|---|---|
| dense stipple | >75% |
| open dots | 50-75% |
| hatched | 25-50% |
| triangles/dots | <25% |

| AB | Pathogen | Pathogen # | Bs1 | Bs1 + AB |
|---|---|---|---|---|
| Gentamicin/Neomycin | E.coli | p2 | -7.238095238 | 87.63838 |
| Gentamicin/Neomycin | E.coli | p3 | 2.658486708 | 1.553398 |
| Gentamicin/Neomycin | E.coli | p4 | -6.167400881 | 84.64491 |
| Gentamicin/Neomycin | E.coli | p5 | -31.88976378 | -15.5303 |
| Gentamicin/Neomycin | E.coli | p6 | 2.697095436 | 5.954825 |
| Gentamicin/Neomycin | E.coli | p11 | -6.794055202 | 74.93606 |
| Gentamicin/Neomycin | C.perfringens | p60 | -5.56621881 | 0.672269 |
| Gentamicin/Neomycin | C.perfringens | p61 | -0.346020761 | 7.371795 |
| Gentamicin/Neomycin | C.perfringens | p63 | -3.066439523 | 7.142857 |
| Gentamicin/Neomycin | C.perfringens | p64 | 3.168316832 | 6.785714 |
| Gentamicin/Neomycin | C.perfringens | p65 | 5.778491172 | 3.322785 |
| Gentamicin/Neomycin | C.perfringens | p66 | 11.14551084 | 9.821429 |
| Tylosin | E.coli | p58 | 35.05402161 | 26.50064 |
| Tylosin | E.coli | p59 | 21.44647333 | 17.79463 |
| Tylosin | E.coli | p21 | -6.959498003 | 12.11153 |
| Tylosin | E.coli | p64 | 11.60714286 | 12.53532 |
| Tylosin | E.coli | p65 | 6.094060499 | 5.484222 |
| Tylosin | E.coli | p66 | 3.173029251 | 11.36792 |
| Tilmicosin | E.coli | p1 | 11.21981046 | 25.01629 |
| Tilmicosin | E.coli | p10 | -1.50989594 | 48.36066 |
| Tilmicosin | E.coli | p11 | 13.44788943 | 7.01725 |
| Tilmicosin | E.coli | p13 | -3.796477495 | 25.80331 |
| Tilmicosin | E.coli | p41 | 12.92042658 | 26.68024 |
| Tilmicosin | E.coli | p58 | 1.95035461 | 52.49674 |

FIG. 6

| Bs2 | Bs2 + AB | Bs3 | Bs3 + AB | Bs4 | Bs4 + AB | Bs5 | Bs5 + AB | Bs6 | Bs6 + AB | Bs7 | Bs7 + AB | Bs8 | Bs8 + AB | AB Control |
|---|---|---|---|---|---|---|---|---|---|---|---|---|---|---|
| 34.47619 | 81.54982 | 36.7619 | 84.50185 | 79.2381 | 79.7048 | 59.2381 | 81.18081 | 31.42857 | 85.97786 | 65.14286 | 85.42435 | -3.42857 | 88.00738 | 87.638376 |
| 69.52965 | 80 | -59.3047 | 80.38835 | 86.50307 | 78.83495 | 83.02658 | 79.02913 | 61.34969 | 80.19417 | 84.86708 | 85.43689 | 2.658487 | 10.67961 | 10.8737864 |
| 70.92511 | 80.6142 | 51.32159 | 82.91747 | 82.37885 | 78.69482 | 77.97357 | 78.88676 | 59.2511 | 83.30134 | 80.837 | 85.02879 | -5.28634 | 86.75624 | 86.5642994 |
| 45.27559 | 54.92424 | 25.19685 | 61.74242 | 71.25984 | 59.09091 | 69.68504 | 60.60606 | 42.51969 | 64.77273 | 64.56693 | 70.45455 | 22.04724 | -9.4697 | -23.863636 |
| 65.9751 | 77.82341 | 54.77178 | 78.64476 | 86.30705 | 78.43943 | 82.78008 | 77.61807 | 59.54357 | 81.72485 | 82.36515 | 83.36756 | 0.207469 | 10.47228 | 11.2936345 |
| 46.70913 | 74.1688 | -55.2017 | 77.74936 | 78.55626 | 72.37852 | 40.55202 | 72.37852 | 30.57325 | 79.28389 | 70.06369 | 80.05115 | -4.88323 | 47.57033 | 74.936061 |
| 83.68522 | 85.21008 | 85.79655 | 86.55462 | 43.37812 | 83.5294 | 61.80422 | 83.5294 | 80.42226 | 88.90756 | 88.86756 | 89.41176 | -8.25336 | -9.41176 | -7.9391892 |
| 83.391 | 84.13462 | 70.93426 | 87.98077 | 34.77509 | 83.33333 | 31.31488 | 84.61538 | 86.15917 | 89.42308 | 64.01384 | 87.17949 | -3.2872 | -1.44231 | -4.9520767 |
| 90.45997 | 86.34921 | 72.5724 | 87.14286 | 38.50085 | 85.07937 | 79.72743 | 82.69841 | 81.60136 | 88.4127 | 53.0494 | 87.61905 | -10.2215 | -8.4127 | -4.494382 |
| 77.22772 | 84.64286 | 73.26733 | 86.78571 | 81.9802 | 82.85714 | 75.64356 | 83.21429 | 70.29703 | 88.92857 | 60.59406 | 88.21429 | -0.39604 | -8.03571 | -15.34296 |
| 62.75929 | 86.07595 | 64.04494 | 87.18354 | 27.28732 | 84.96835 | -5.77849 | 83.21429 | 75.92295 | 90.03165 | 74.1573 | 89.71519 | -1.1236 | -3.00633 | 1.34680135 |
| 76.78019 | 86.30952 | 53.09598 | 87.79762 | 65.47988 | 85.41667 | 78.01858 | 85.71429 | 80.03096 | 90.17857 | 75.85139 | 89.88095 | 13.93189 | -1.04167 | -7.5342466 |
| 78.7515 | 76.24521 | 79.08163 | 77.29885 | 75.9904 | 77.45849 | 79.11164 | 76.6922 | 74.57983 | 76.37292 | 73.76951 | 73.69003 | 14.58583 | 35.69604 | 18.7739464 |
| 81.88328 | 75.90432 | 80.25421 | 67.15286 | 80.52274 | 69.91443 | 81.43573 | 78.91871 | 77.92696 | 80.00778 | 74.25707 | 72.3065 | 21.06634 | 13.20498 | 32.9638273 |
| 53.29911 | 64.21595 | 62.17912 | 74.78245 | 36.9652 | 49.88457 | 54.53508 | 62.13816 | 45.63605 | 51.57166 | 36.52786 | 45.49814 | -12.0175 | 6.464216 | 12.3601492 |
| 70.35189 | 76.13666 | 76.20793 | 81.68508 | 63.52416 | 58.30979 | 71.13971 | 68.6617 | 69.17017 | 60.8785 | 58.61345 | 56.58875 | -2.57353 | 5.856666 | 4.5723927 |
| 76.79399 | 75.47334 | 82.00486 | 79.4124 | 66.57099 | 64.24374 | 76.57319 | 74.12405 | 70.69993 | 68.4222 | 70.10378 | 65.83243 | 2.759991 | 2.698585 | -7.508161 |
| 76.67328 | 75.68396 | 79.72236 | 79.95283 | 64.55131 | 68.56132 | 75.9296 | 74.90566 | 69.50917 | 73.4434 | 61.97323 | 64.08019 | -4.09023 | 9.198113 | 14.0801887 |
| 31.45827 | 70.39088 | 54.66218 | 75.27687 | 32.34485 | 72.08469 | 55.54876 | 73.38762 | 25.46622 | 71.75896 | 16.50871 | 67.557 | 13.05411 | 44.59283 | 26.3517915 |
| 47.78617 | 76.15144 | 62.13018 | 81.36222 | 39.60416 | 73.55582 | 51.70373 | 80.77674 | 40.95083 | 78.61046 | 30.15711 | 74.35597 | 4.468476 | 44.55504 | 46.5651855 |
| 84.98319 | 88.76235 | 83.33956 | 89.33177 | 79.86552 | 90.06867 | 89.18566 | 88.31017 | 31.78932 | 88.24318 | 19.66754 | 96.31172 | 27.77363 | 36.19159 | 22.7265115 |
| 49.5499 | 66.67478 | 44.34442 | 72.07887 | 31.23288 | 69.52288 | 47.49511 | 71.03213 | 35.45988 | 61.80623 | 41.60047 | 53.50536 | -10.7632 | 19.54722 | -45.861733 |
| 41.48893 | 74.93057 | 53.93765 | 79.57786 | 17.47334 | 73.1046 | 49.79491 | 76.63396 | 21.47252 | 74.67136 | 11.34126 | 64.43251 | 0.246103 | 21.03314 | 33.4382522 |
| 69.63652 | 83.63005 | 74.60106 | 84.15111 | 55.51862 | 82.08858 | 87.52216 | 84.45506 | 59.50798 | 82.54451 | 50.35461 | 84.69388 | 0.886525 | 32.91359 | 21.6239687 |

{ 6 Finalist Bacillus

*FIG. 6 (cont.)*

| Pathogen | Pathogen # | Antibiotic | Bs2 | Bs3 | Bs4 | Bs5 | BS 9 | BS 57 | BS 71 | BS 126 | Anti Control |
|---|---|---|---|---|---|---|---|---|---|---|---|
| E.coli | p1 | Mecadox | 79.53057 | 74.01747 | 76.17904 | 59.29039 | 48.75027 | 72.76223 | 47.92779 | 55.92351 | 1.944505 |
| E.coli | p2 | | 75.36409 | 71.93734 | 71.21527 | 74.93575 | 39.04962 | 53.12993 | 45.4673 | 42.66607 | 6.483327 |
| E.coli | p3 | | 77.75404 | 76.48152 | 79.1566 | 79.43526 | 47.48809 | 76.49921 | 62.41064 | 63.53739 | 5.94868 |
| E.coli | p4 | | 83.13918 | 72.70591 | 77.91743 | 77.03863 | 45.74448 | 75.43876 | 60.86998 | 68.58333 | 12.04188 |
| E.coli | p5 | | 63.03264 | 43.733 | 76.15594 | 73.10743 | 41.88124 | 71.85497 | 52.63269 | 66.39804 | 4.063543 |
| E.coli | p6 | | 46.66849 | 34.08178 | 69.38664 | 42.68894 | 51.34565 | 70.05423 | 59.55011 | 66.50397 | 8.785556 |
| E.coli | p7 | | 66.14948 | 59.52797 | 52.53497 | 64.57605 | 50.47563 | 62.80681 | 14.75044 | 4.817276 | 16.29812 |
| E.coli | p8 | | 71.77985 | 75.5547 | 76.1118 | 74.16194 | 67.98053 | 89.96794 | 72.8719 | 79.59631 | 45.80027 |
| E.coli | p9 | | 54.77142 | 71.36041 | 55.23746 | 71.81536 | 50.28739 | 58.89691 | 50.84994 | 45.84256 | 1.673736 |
| E.coli | p10 | | 63.35848 | 58.14256 | 61.84964 | 58.05151 | 29.79844 | 53.77557 | 32.17509 | 39.11529 | 1.286533 |
| E.coli | p11 | | 73.8027 | 48.23987 | 69.52517 | 65.80025 | 28.37659 | 52.17774 | 33.86127 | 45.90677 | 31.6947 |
| E.coli | p12 | | 51.86514 | 66.36777 | 51.54232 | 61.2506 | 57.88232 | 53.0861 | 55.94286 | 53.31447 | 35.58378 |
| E.coli | p13 | | 53.34113 | 53.35575 | 56.19243 | 52.06902 | 34.40638 | 47.01713 | 33.54991 | 31.7401 | 24.78756 |
| E.coli | p14 | | 72.19626 | 65.35514 | 68.43925 | 69.04673 | 46.94202 | 65.98295 | 47.2511 | 51.82547 | 13.88971 |
| E.coli | p15 | | 79.87344 | 72.68606 | 74.85833 | 73.67775 | 52.64603 | 70.45347 | 62.51065 | 57.58826 | 3.70127 |
| E.coli | p16 | | 81.50467 | 70.40748 | 75.64782 | 73.74049 | 35.26225 | 74.92403 | 37.01942 | 49.69913 | 28.50941 |
| E.coli | p17 | | 51.84023 | 45.46362 | 58.64479 | 46.7903 | 34.08611 | 34.19984 | 38.63526 | 37.81043 | 9.88881 |
| E.coli | p18 | | 25.34835 | 14.9456 | 34.49132 | 15.80454 | 33.25419 | 36.65717 | 40.89902 | 30.1992 | -0.47031 |
| E.coli | p19 | | 75.49655 | 55.05045 | 68.40149 | 69.54859 | 49.47559 | 73.85584 | 62.15675 | 63.89846 | 20.30446 |
| E.coli | p20 | | 77.43609 | 71.6798 | 76.93638 | 77.0517 | 52.02486 | 75.72047 | 60.82125 | 63.21896 | 4.895039 |
| E.coli | p21 | | 75.07968 | 63.53449 | 68.56174 | 69.25054 | 49.31716 | 73.47126 | 58.12271 | 58.9297 | 19.97196 |
| E.coli | p22 | | 73.26366 | 69.43494 | 74.10524 | 70.89614 | 50.24915 | 67.88918 | 54.7339 | 58.95123 | 3.153031 |
| E.coli | p23 | | 76.07178 | 69.41902 | 75.44639 | 71.94779 | 46.35202 | 62.15339 | 48.6234 | 50.0923 | 5.293802 |
| E.coli | p24 | | 72.45577 | 54.10881 | 69.59292 | 38.43447 | 47.62942 | 71.17688 | 52.61803 | 49.56265 | 9.691051 |
| E.coli | p25 | | 64.71199 | 67.40321 | 70.42493 | 60.82153 | 44.83134 | 67.96914 | 57.68127 | 55.37182 | 2.942262 |
| E.coli | p26 | | 73.70905 | 73.61465 | 69.35712 | 69.45152 | 56.95364 | 65.39488 | 62.93368 | 56.20525 | 3.77307 |
| E.coli | p27 | | 72.64851 | 64.78484 | 62.34768 | 69.14509 | 51.93232 | 65.56868 | 61.93432 | 55.06444 | 3.58228 |
| E.coli | p28 | | 68.40419 | 48.99614 | 51.57885 | 46.58309 | 24.32649 | 57.34266 | 39.13791 | 51.89942 | 1.903817 |
| E.coli | p29 | | 62.40523 | 54.47309 | 48.94807 | 59.91281 | 37.31009 | 56.86457 | 47.14326 | 41.98952 | 20.25953 |
| E.coli | p30 | | 68.63316 | 59.55848 | 61.35275 | 59.0418 | 16.07839 | 52.21958 | 37.09398 | 41.22422 | 6.99241 |
| E.coli | p31 | | | | | | | | | | |

FIG. 9

METHODS OF INHIBITION WITH MICROBIAL STRAINS AND ANTIBIOTICS

CROSS-REFERENCE TO RELATED APPLICATIONS

This application is a national stage entry under 35 USC § 371 (b) of PCT International Application No. PCT/US2020/047390, filed Aug. 21, 2020, which claims priority under 35 U.S.C. § 119 (e) to U.S. Provisional Application Ser. No. 62/890,267 filed on Aug. 22, 2019, the disclosure of which is expressly incorporated by reference herein.

FIELD OF THE DISCLOSURE

The invention relates to direct-fed microbials for use in *E. coli* and/or *Clostridium* inhibition in animals in combination with antibiotics. More particularly, the invention relates to isolated *Bacillus* strains 2, 3, 4, 5, 6, 7, 9, 57, 71, and 126 and strains having all of the identifying characteristics of these strains, for a use comprising the above-mentioned use.

BACKGROUND AND SUMMARY OF THE INVENTION

The present invention relates to direct-fed microbial (DFM) compositions and methods for *E. coli* and/or *Clostridium* inhibition in an animal. An animal's gastrointestinal tract is constantly challenged by large numbers of bacteria, viruses, fungi, and protozoa found in feed, bedding, and the environment. The gastrointestinal tract has a sophisticated system to counter these potential pathogens consisting of physical, chemical, and immunological lines of defense. Beneficial bacteria are an important part of this system because they provide animals with bacteria that assist in establishment (or reestablishment) of a normal bacterial profile, they strengthen the animal's immune system, and they help to fight disease.

Antibiotic resistance is an increasingly important issue in human medicine, as well as in animal agriculture. The Food and Drug Administration reported that in 2016 the U.S. swine industry purchased about 6.9 million pounds of medically important antibiotics, which emphasizes the importance of preventing the development of antibiotic resistant organisms in the animal agricultural industry. Methods are being developed in an effort to combat antibiotic resistance, but little has been done to utilize synergistic direct-fed microbials (e.g., probiotics) as tools to combat antibiotic resistance.

Applicants have developed direct-fed microbials that result in *E. coli* and/or *Clostridium* inhibition in animals in combination with antibiotics. The direct-fed microbials and antibiotics and compositions comprising the direct-fed microbials and antibiotics described herein offer a commercial benefit by providing *E. coli* and/or *Clostridium* inhibition in animals, such as agricultural animals.

Methods are provided for inhibiting *E. coli* and/or *Clostridium* in animals. In various embodiments, the animal can be selected from the group consisting of a poultry species, a porcine species, a caprine species, a bovine species, an ovine species, an equine species, and a companion animal. In the embodiment where the animal is a poultry species, the poultry species can be selected from the group consisting of a broiler, a chicken, a layer, a breeder, a turkey, a turkey poult, a gosling, a duckling, a guineakeet, a pullet, a hen, a rooster, a cockerel, and a capon. In the embodiment where the animal is a porcine species, the porcine species can be selected from the group consisting of a grow finish pig, a nursery pig, a sow, and a breeding stock pig.

In one embodiment, a method of feeding an animal is provided. The method comprises the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* and/or *Clostridium* inhibition in the animal.

In another embodiment, a method of controlling a detrimental effect of *E. coli* and/or *Clostridium* is provided. The method comprises the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* and/or *Clostridium* in the animal.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of feeding an animal, the method comprising the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* and/or *Clostridium* inhibition in the animal.

2. The method of clause 1 wherein the animal is selected from the group consisting of a poultry species, a porcine species, a caprine species, a bovine species, an ovine species, an equine species, and a companion animal.

3. The method of any one of clauses 1 to 2 wherein the *E. coli* and/or *Clostridium* inhibition prevents *E. coli* and/or *Clostridium* disease in the animal.

4. The method of any one of clauses 1 to 2 wherein the *E. coli* and/or *Clostridium* inhibition reduces *E. coli* and/or *Clostridium* disease in the animal.

5. The method of any one of clauses 1 to 4 wherein the animal is a porcine species and the porcine species is selected from the group consisting of a grow finish pig, a nursery pig, a sow, and a breeding stock pig.

6. The method of any one of clauses 1 to 5 wherein the *Bacillus* strain produces an enzyme selected from the group consisting of an $\alpha$-galactosidase, a protease, a lipase, an amylase, a xylanase, a cellulase, and combinations thereof.

7. The method of any one of clauses 1 to 6 further comprising the step of administering to the animal another different bacterial strain selected from the group consisting of another *Bacillus* strain, a lactic acid bacterial strain, and combinations thereof.

8. The method of any one of clauses 1 to 7 wherein the strain administered is *Bacillus* strain 2 (NRRL No. B-67709).

9. The method of any one of clauses 1 to 7 wherein the strain administered is *Bacillus* strain 3 (NRRL No. B-67710).

10. The method of any one of clauses 1 to 7 wherein the strain administered is *Bacillus* strain 4 (NRRL No. B-67711).

11. The method of any one of clauses 1 to 7 wherein the strain administered is *Bacillus* strain 5 (NRRL No. B-67712).

12. The method of any one of clauses 1 to 7 wherein the strain administered is *Bacillus* strain 6 (NRRL No. B-67714).

13. The method of any one of clauses 1 to 7 wherein the strain administered is *Bacillus* strain 7 (NRRL No. B-67713).

14. The method of any one of clauses 1 to 13 wherein the *Bacillus* strain is administered in the feed composition at a dose of about $1.0\times10^3$ CFU/gram of the feed composition to about $5.0\times10^{12}$ CFU/gram of the feed composition.

15. The method of any one of clauses 1 to 13 wherein the *Bacillus* strain is administered in the feed composition at a dose of about $1.0\times10^3$ CFU/gram of the feed composition to about $1.0\times10^7$ CFU/gram of the feed composition.

16. The method of any one of clauses 1 to 13 wherein the *Bacillus* strain is administered in the feed composition at a dose greater than about $7.0\times10^4$ CFU/gram of the feed composition.

17. The method of any one of clauses 1 to 16 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

18. The method of any one of clauses 1 to 17 wherein the animal is a sow and the *Bacillus* strain is administered during lactation.

19. The method of any one of clauses 1 to 17 wherein the animal is a sow and the *Bacillus* strain is administered during gestation.

20. The method of any one of clauses 1 to 19 wherein the feed composition is administered daily to the animal.

21. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

22. The method of any one of clauses 1 to 21 wherein the antibiotic is selected from the group consisting of tylosin, tilmicosin, avilamycin, gentamycin, carbadox, tiamulin, and neomycin.

23. A method of controlling a detrimental effect of *E. coli* and/or *Clostridium*, the method comprising the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* and/or *Clostridium* in the animal.

24. The method of clause 23 wherein the animal is selected from the group consisting of a poultry species, a porcine species, a caprine species, a bovine species, an ovine species, an equine species, and a companion animal.

25. The method of any one of clauses 23 to 24 wherein controlling the detrimental effect of the *E. coli* and/or *Clostridium* is inhibiting *E. coli* and/or *Clostridium* disease in the animal.

26. The method of any one of clauses 23 to 24 wherein controlling the detrimental effect of the *E. coli* and/or *Clostridium* is reducing *E. coli* and/or *Clostridium* disease in the animal.

27. The method of any one of clauses 23 to 26 wherein the animal is a porcine species and the porcine species is selected from the group consisting of a grow finish pig, a nursery pig, a sow, and a breeding stock pig.

28. The method of any one of clauses 23 to 27 wherein the *Bacillus* strain produces an enzyme selected from the group consisting of an α-galactosidase, a protease, a lipase, an amylase, a xylanase, a cellulase, and combinations thereof.

29. The method of any one of clauses 23 to 28 further comprising the step of administering to the animal another different bacterial strain selected from the group consisting of another *Bacillus* strain, a lactic acid bacterial strain, and combinations thereof.

30. The method of any one of clauses 23 to 29 wherein the strain administered is *Bacillus* strain 2 (NRRL No. B-67709).

31. The method of any one of clauses 23 to 29 wherein the strain administered is *Bacillus* strain 3 (NRRL No. B-67710).

32. The method of any one of clauses 23 to 29 wherein the strain administered is *Bacillus* strain 4 (NRRL No. B-67711).

33. The method of any one of clauses 23 to 29 wherein the strain administered is *Bacillus* strain 5 (NRRL No. B-67712).

34. The method of any one of clauses 23 to 29 wherein the strain administered is *Bacillus* strain 6 (NRRL No. B-67714).

35. The method of any one of clauses 23 to 29 wherein the strain administered is *Bacillus* strain 7 (NRRL No. B-67713).

36. The method of any one of clauses 23 to 35 wherein the *Bacillus* strain is administered in the feed composition at a dose of about $1.0 \times 10^3$ CFU/gram of the feed composition to about $5.0 \times 10^{12}$ CFU/gram of the feed composition.

37. The method of any one of clauses 23 to 35 wherein the *Bacillus* strain is administered in the feed composition at a dose of about $1.0 \times 10^3$ CFU/gram of the feed composition to about $1.0 \times 10^7$ CFU/gram of the feed composition.

38. The method of any one of clauses 23 to 35 wherein the *Bacillus* strain is administered in the feed composition at a dose greater than about $7.0 \times 10^4$ CFU/gram of the feed composition.

39. The method of any one of clauses 23 to 38 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

40. The method of any one of clauses 23 to 39 wherein the animal is a sow and the *Bacillus* strain is administered during lactation.

41. The method of any one of clauses 23 to 39 wherein the animal is a sow and the *Bacillus* strain is administered during gestation.

42. The method of any one of clauses 23 to 41 wherein the feed composition is administered daily to the animal.

43. The method of clause 23 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

44. The method of any one of clauses 23 to 43 wherein the antibiotic is selected from the group consisting of tylosin, tilmicosin, avilamycin, gentamycin, carbadox, tiamulin, and neomycin.

45. A method of feeding an animal, the method comprising the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

46. The method of clause 45 wherein the animal is selected from the group consisting of a poultry species, a porcine species, a caprine species, a bovine species, an ovine species, an equine species, and a companion animal.

47. The method of any one of clauses 45 to 46 wherein the animal is a sow.

48. The method of any one of clauses 45 to 46 wherein the animal is a chicken.

49. The method of any one of clauses 45 to 48 wherein the animal is a porcine species and the porcine species is selected from the group consisting of a grow finish pig, a nursery pig, a sow, and a breeding stock pig.

50. The method of any one of clauses 45 to 49 wherein the *Bacillus* strain produces an enzyme selected from the group consisting of an α-galactosidase, a protease, a lipase, an amylase, a xylanase, a cellulase, and combinations thereof.

51. The method of any one of clauses 45 to 50 further comprising the step of administering to the animal another different bacterial strain selected from the group consisting of another *Bacillus* strain, a lactic acid bacterial strain, and combinations thereof.

52. The method of any one of clauses 45 to 51 wherein the strain administered is *Bacillus* strain 2 (NRRL No. B-67709).

53. The method of any one of clauses 45 to 51 wherein the strain administered is *Bacillus* strain 3 (NRRL No. B-67710).

54. The method of any one of clauses 45 to 51 wherein the strain administered is *Bacillus* strain 4 (NRRL No. B-67711).

55. The method of any one of clauses 45 to 51 wherein the strain administered is *Bacillus* strain 5 (NRRL No. B-67712).

56. The method of any one of clauses 45 to 51 wherein the strain administered is *Bacillus* strain 6 (NRRL No. B-67714).

57. The method of any one of clauses 45 to 51 wherein the strain administered is *Bacillus* strain 7 (NRRL No. B-67713).

58. The method of any one of clauses 45 to 57 wherein the *Bacillus* strain is administered in the feed composition at a dose of about $1.0 \times 10^3$ CFU/gram of the feed composition to about $5.0 \times 10^{12}$ CFU/gram of the feed composition.

59. The method of any one of clauses 45 to 57 wherein the *Bacillus* strain is administered in the feed composition at a dose of about $1.0 \times 10^3$ CFU/gram of the feed composition to about $1.0 \times 10^7$ CFU/gram of the feed composition.

60. The method of any one of clauses 45 to 57 wherein the *Bacillus* strain is administered in the feed composition at a dose greater than about $7.0 \times 10^4$ CFU/gram of the feed composition.

61. The method of any one of clauses 45 to 60 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

62. The method of any one of clauses 45 to 61 wherein the animal is a sow and the *Bacillus* strain is administered during lactation.

63. The method of any one of clauses 45 to 61 wherein the animal is a sow and the *Bacillus* strain is administered during gestation.

64. The method of any one of clauses 45 to 63 wherein the feed composition is administered daily to the animal.

65. The method of clause 45 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

66. The method of any one of clauses 45 to 65 further comprising the step of administering an antibiotic wherein the antibiotic is selected from the group consisting of tylosin, tilmicosin, avilamycin, gentamycin, carbadox, tiamulin, and neomycin.

67. The method of any one of clauses 1 to 66 wherein the *Bacillus* strain has an effect selected from the group consisting of maintaining microbial balance in the gut of the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.

68. The method of any one of clauses 1 to 7, 14 to 29, 36 to 51, or 58 to 67 wherein the strain administered is *Bacillus* strain 9 (NRRL No. B-67866).

69. The method of any one of clauses 1 to 7, 14 to 29, 36 to 51, or 58 to 67 wherein the strain administered is *Bacillus* strain 57 (NRRL No. B-67870).

70. The method of any one of clauses 1 to 7, 14 to 29, 36 to 51, or 58 to 67 wherein the strain administered is *Bacillus* strain 71 (NRRL No. B-67867).

71. The method of any one of clauses 1 to 7, 14 to 29, 36 to 51, or 58 to 67 wherein the strain administered is *Bacillus* strain 126 (NRRL No. B-67868).

72. A commercial package comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

73. A feed additive for an animal feed comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

74. An additive for the drinking water of an animal comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

75. An animal feed composition comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

76. The commercial package, feed additive, feed composition, or additive for the drinking water of the animal of any one of clauses 72 to 75 wherein the *Bacillus* strain causes an effect selected from the group consisting of preventing *E. coli* and/or *Clostridium* disease, reducing *E. coli* and/or *Clostridium* disease, maintaining the microbial balance of the animal, and combinations thereof.

77. The commercial package, feed additive, feed composition, or additive for the drinking water of the animal of any one of clauses 72 to 75, wherein the *Bacillus* strain reduces *E. coli* and/or *Clostridium* disease in the animal.

78. The feed additive or additive for the drinking water of the animal of clause 73 or 74 in the form of a concentrate.

79. The feed additive or additive for the drinking water of the animal of clause 73 or 74 in the form of a superconcentrate.

80. The feed additive, feed composition, or additive for the drinking water of the animal of any one of clauses 73 to 79 in dry form.

81. The feed additive, feed composition, or additive for the drinking water of the animal of any one of clauses 73 to 80 in pelleted form.

82. The commercial package, feed additive, feed composition, or additive for the drinking water of the animal of any one of clauses 72 to 79 wherein the strains are in a form selected from the group consisting of a powder, a pellet, a liquid, a liquid drench, a freeze-dried composition, a capsule, a top-dressing, a paste, and a gel.

83. The commercial package, feed additive, additive for the drinking water of the animal, or feed composition of any one of clauses 72 to 82 further comprising a carrier for the *Bacillus* strains.

84. The commercial package, feed additive, additive for the drinking water of the animal, or feed composition of clause 83 wherein the carrier is selected from the group consisting of a bran, rice hulls, a salt, mineral oil, a dextrin (e.g., maltodextrin), whey, sugar, sucrose, limestone, yeast culture, dried starch, sodium silico aluminate, silicon dioxide, polypropylene glycol, polysorbate 80, vegetable oil, and combinations thereof.

85. The commercial package, feed additive, additive for the drinking water of the animal, or feed composition of any one of clauses 72 to 84 in a bag.

86. The commercial package, feed additive, additive for the drinking water of the animal, or feed composition of clause 85 wherein the bag is a plastic bag.

87. The commercial package, feed additive, additive for the drinking water of the animal, or feed composition of any one of clauses 72 to 86 further comprising instructions for use of one or more of the *Bacillus* strains.

88. The commercial package, feed additive, feed composition, or additive for the drinking water of the animal of any one of clauses 72 to 87 in a 20-pound bag.

89. The commercial package, feed additive, feed composition, or additive for the drinking water of the animal of any one of clauses 72 to 87 in a 50-pound bag.

90. The commercial package, feed additive, additive for the drinking water of the animal, or feed composition of any one of clauses 72 to 89 in a container for commercial use.

91. The commercial package, feed additive, additive for the drinking water of the animal, or feed composition of clause 90 wherein the container comprises plastic.

92. The commercial package, feed additive, additive for the drinking water of the animal, or feed composition of clause 90 wherein the container comprises paper.

93. The commercial package, feed additive, additive for the drinking water of the animal, or feed composition of any one of clauses 72 to 92 further comprising a binder.

94. The commercial package, feed additive, additive for the drinking water of the animal, or feed composition of clause 93 wherein the binder is selected from the group consisting of clay, yeast cell wall components, aluminum silicate, and glucan, or combinations thereof.

95. The commercial package, feed additive, additive for the drinking water of the animal, or feed composition of any one of clauses 72 to 94 further comprising an exogenously added nutrient component selected from the group consisting of a vitamin, an antibiotic, an enzyme, a water-soluble or water-insoluble monosaccharide, disaccharide, or polysaccharide, a fat, phosphorous, sodium bicarbonate, limestone, calcium, sodium, sulfur, magnesium, potassium, copper, iron, manganese, zinc, fish oil, raw seed, an antioxidant, and a starch.

96. The commercial package, feed additive, additive for the drinking water of the animal, or feed composition of clause 95 wherein the exogenously added nutrient component is an enzyme and the enzyme is selected from the group consisting of a galactosidase, a protease, a lipase, an amylase, a hemicellulase, an arabinoxylanase, a xylanase, a cellulase, an NSPase, a phytase, and combinations thereof.

97. The commercial package, feed additive, additive for the drinking water of the animal, or feed composition of any one of clauses 72 to 96 wherein the *Bacillus* strains are selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

98. The commercial package, feed additive, additive for the drinking water of the animal, or feed composition of any one of clauses 72 to 96 wherein the *Bacillus* strains are selected from the group consisting of *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

99. The commercial package, feed additive, additive for the drinking water of the animal, or feed composition of any one of clauses 72 to 96 wherein the *Bacillus* strains are selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), and combinations thereof.

BRIEF DESCRIPTION OF THE DRAWINGS

FIG. 6 is a heat map of percent inhibition values from 24 of 280 pathogens showing an effective inhibition response when *Bacillus* supernatant and various antibiotics are combined.

FIG. 9 is a heat map of percent inhibition values from all 31 resistant *E. coli* showing an effective inhibition response when eight *Bacillus* supernatants are used in place of Mecadox™.

DETAILED DESCRIPTION OF ILLUSTRATIVE EMBODIMENTS

Figures 1A, 1B:
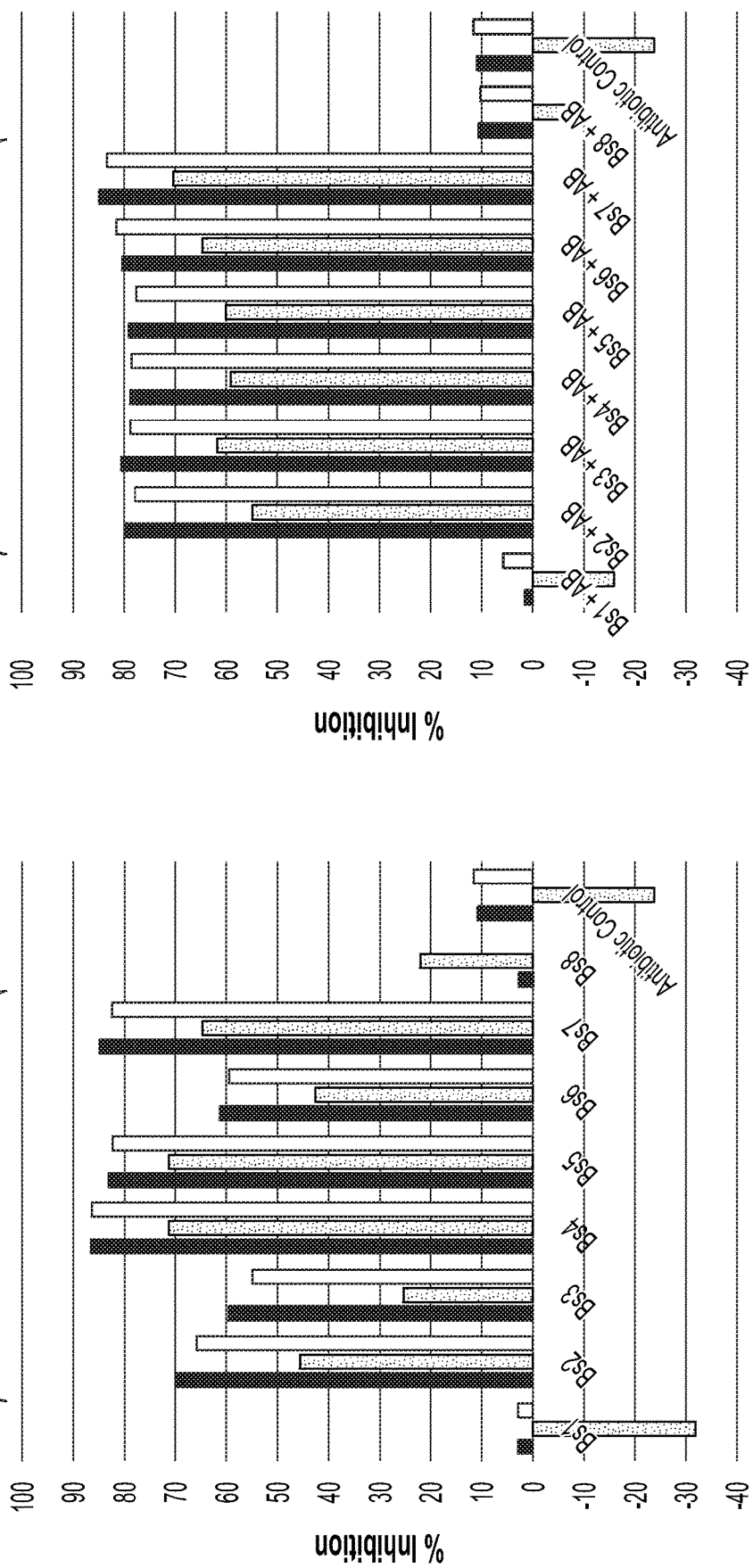
FIGS. 1A and 1B show percent inhibition values from 3 of 50 *E. coli* showing an improved inhibition response when *Bacillus* supernatant and Gentamicin & Neomycin are combined.
Figure 2A:
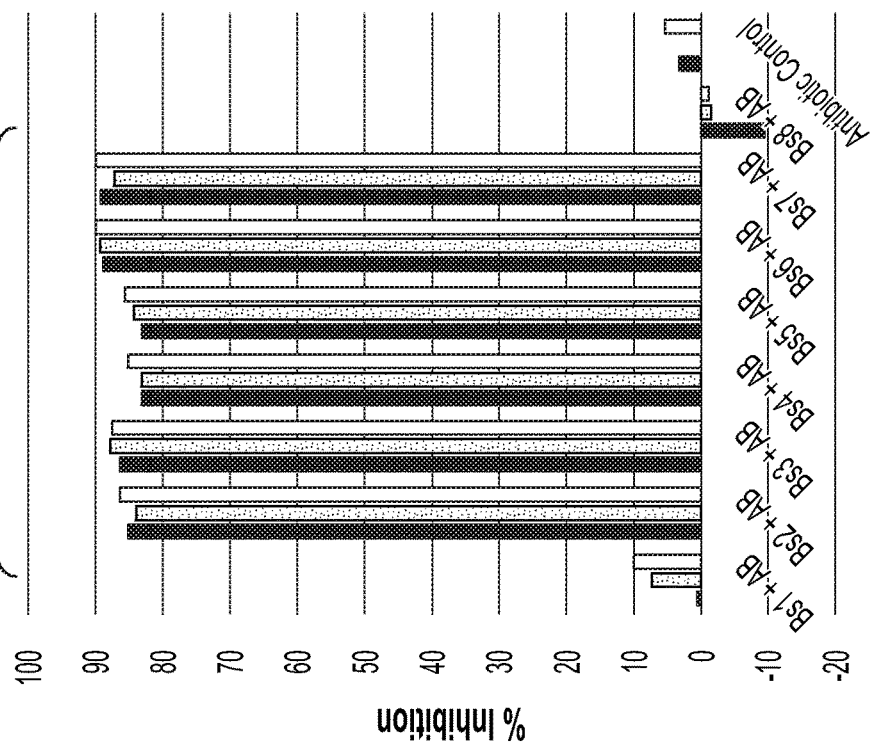
FIGS. 2A and 2B show percent inhibition values from 3 of 66 *C. perfringens* showing an improved inhibition response when *Bacillus* supernatant and Gentamicin & Neomycin are combined.
Figure 2B:
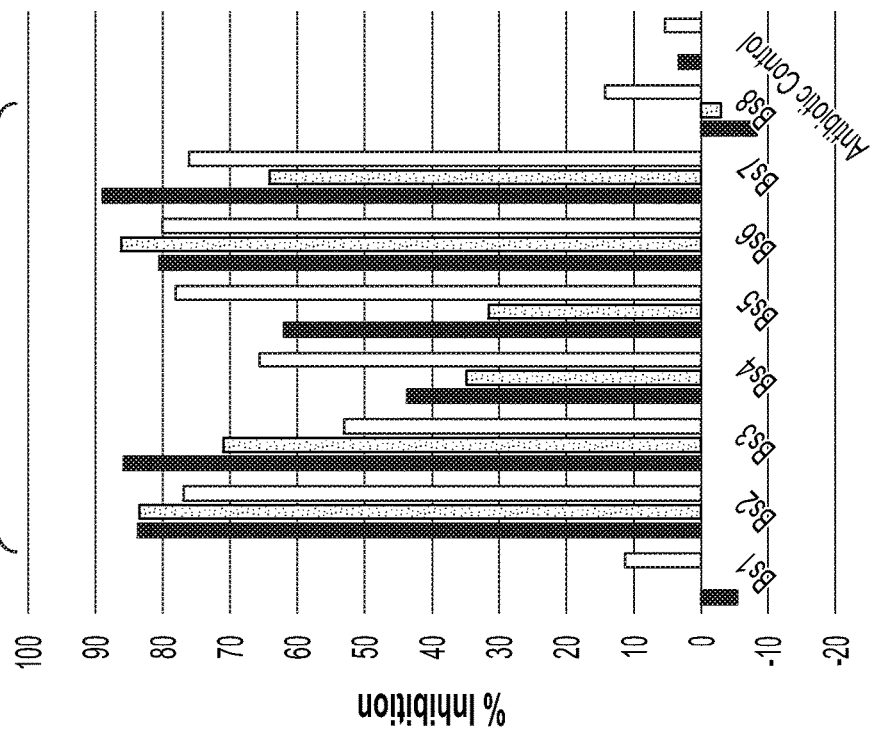
Figure 3B:
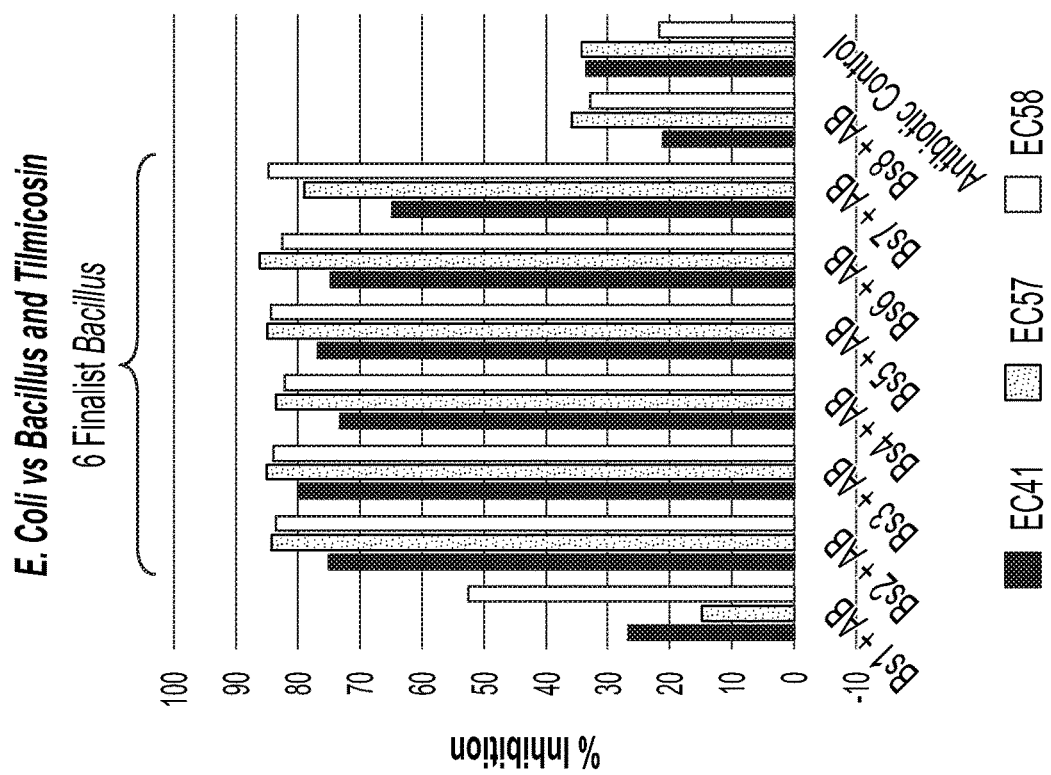
FIGS. 3A and 3B show percent inhibition values from 3 of 64 *E. coli* showing an improved inhibition response when *Bacillus* supernatant and Tilmicosin are combined.
Figure 3A:
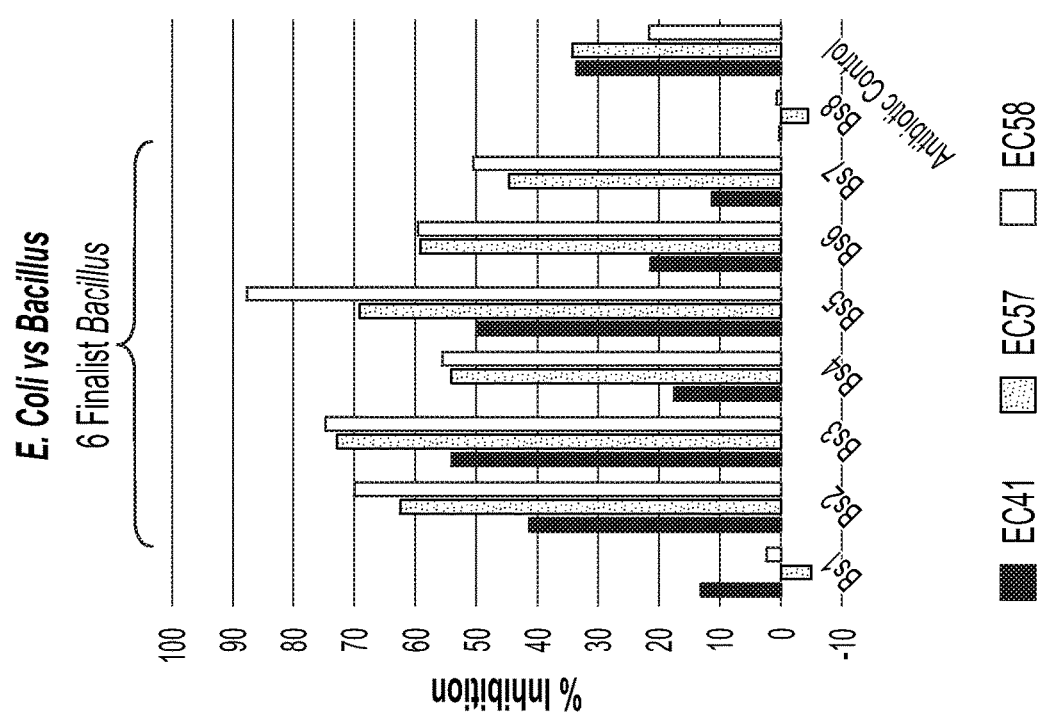
Figure 4B:
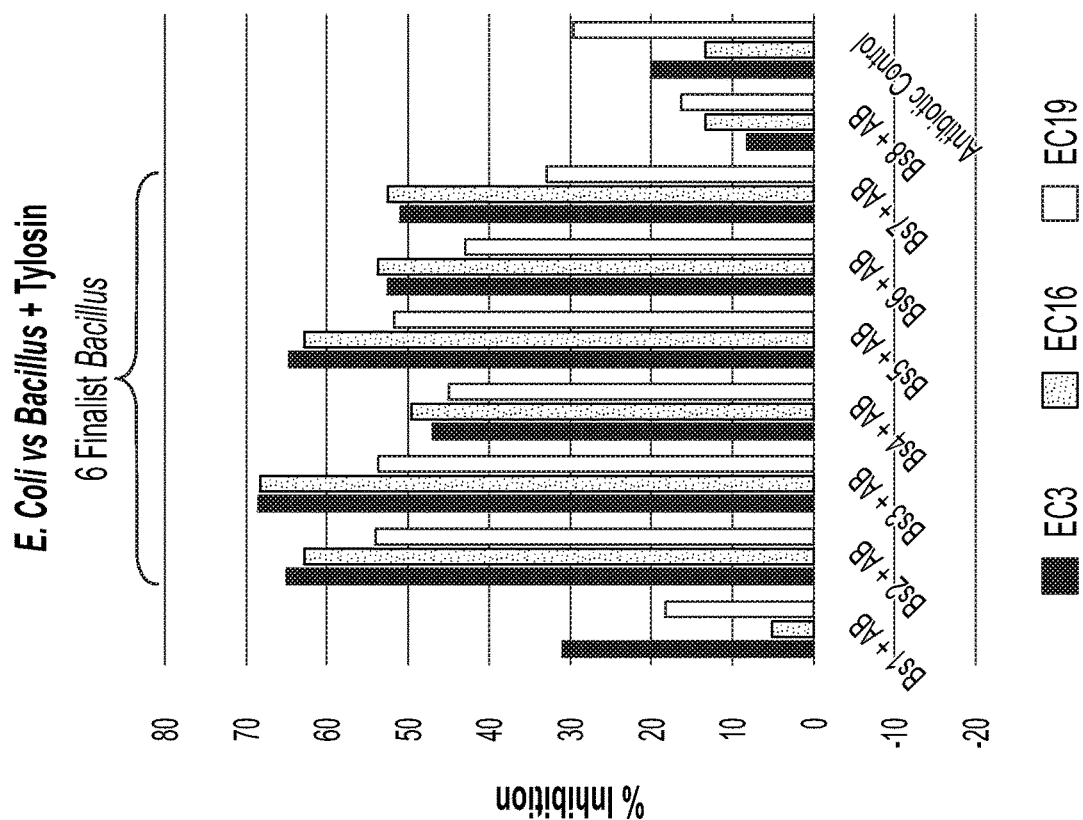
FIGS. 4A and 4B show percent inhibition values from 3 of 68 *E. coli* showing an improved inhibition response when *Bacillus* supernatant and Tylosin are combined.
Figure 4A:
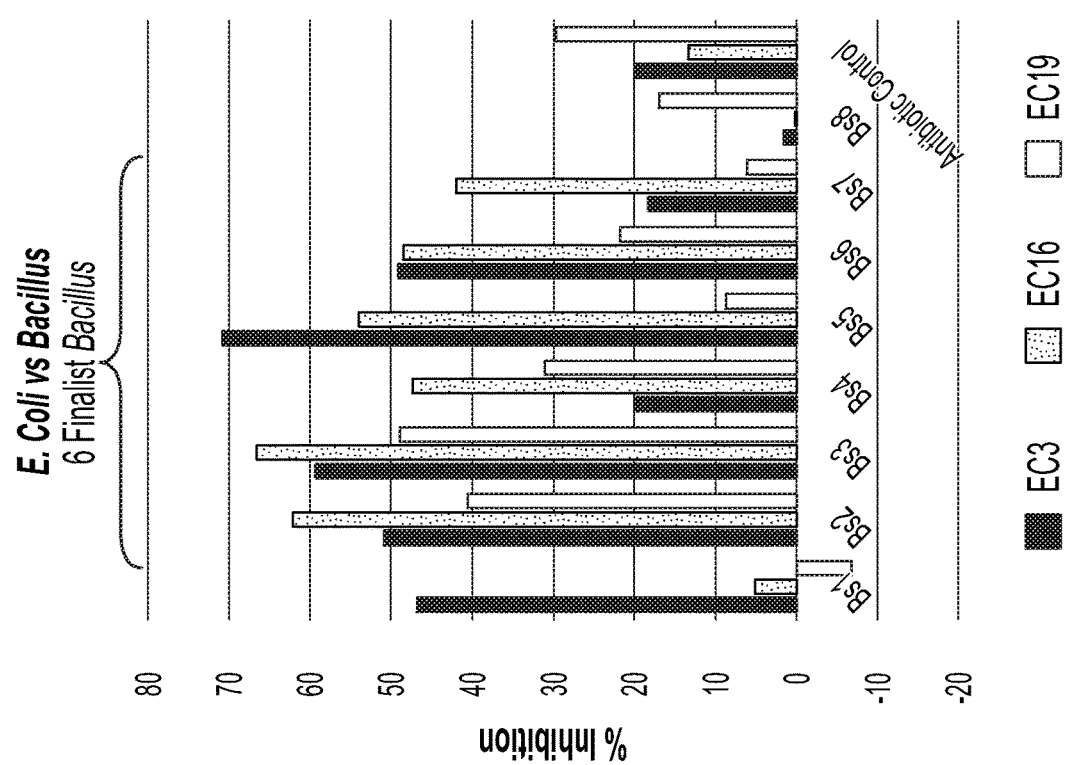
Figure 5B:
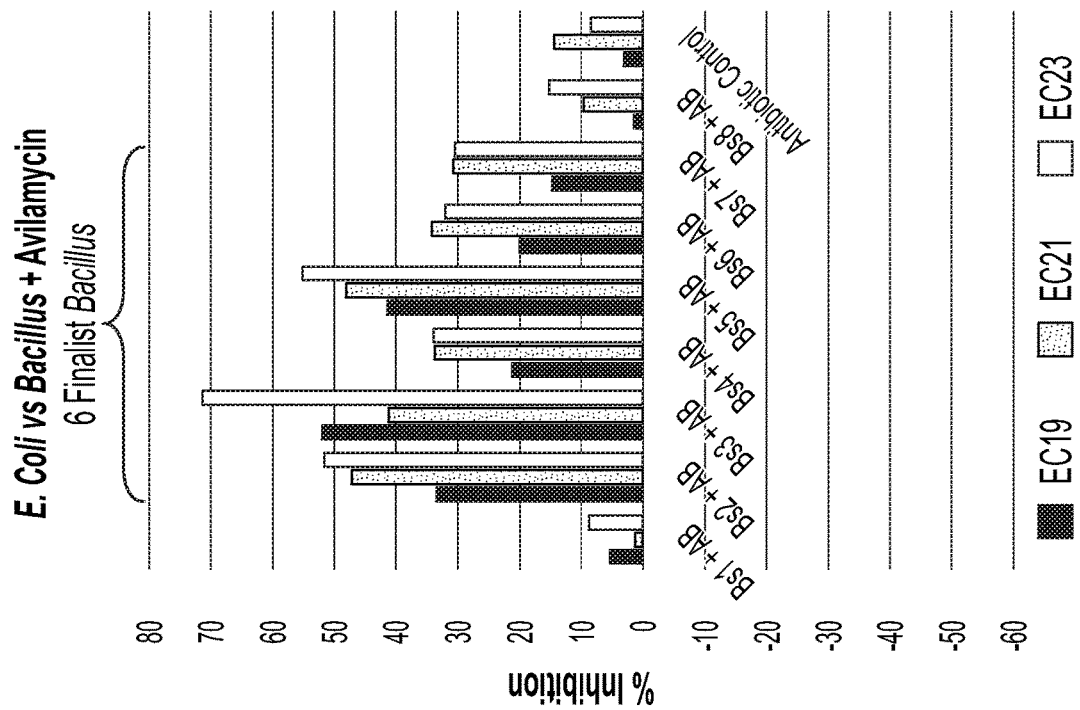
FIGS. 5A and 5B show percent inhibition values from 3 of 32 *E. coli* showing an improved inhibition response when *Bacillus* supernatant and Avilamycin are combined.
Figure 5A:
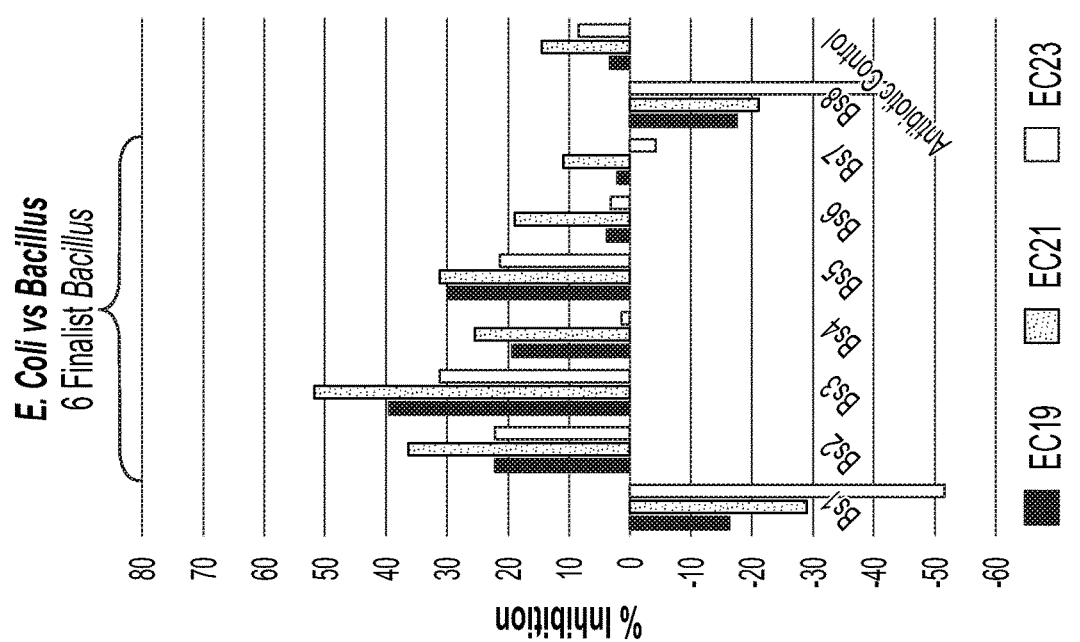

Methods are provided for inhibiting *E. coli* and/or *Clostridium* in animals. In various embodiments, the animal can be selected from the group consisting of a poultry species, a porcine species, a caprine species, a bovine species, an ovine species, an equine species, and a companion animal. In the embodiment where the animal is a poultry species, the poultry species can be selected from the group consisting of a broiler, a chicken, a layer, a breeder, a turkey, a turkey poult, a gosling, a duckling, a guineakeet, a pullet, a hen, a rooster, a cockerel, and a capon. In the embodiment where the animal is a porcine species, the porcine species can be selected from the group consisting of a grow finish pig, a nursery pig, a sow, and a breeding stock pig.

In one embodiment, a method of feeding an animal is provided. The method comprises the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* and/or *Clostridium* inhibition in the animal.

In another embodiment, a method of controlling a detrimental effect of *E. coli* and/or *Clostridium* is provided. The method comprises the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* and/or *Clostridium* in the animal.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

The following clauses, and combinations thereof, provide various additional illustrative aspects of the invention described herein. The various embodiments described in this section titled "DETAILED DESCRIPTION OF ILLUSTRATIVE EMBODIMENTS" are applicable to any of the following embodiments of the invention described in the numbered clauses below.

1. A method of feeding an animal, the method comprising the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No.

B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* and/or *Clostridium* inhibition in the animal.

2. The method of clause 1 wherein the animal is selected from the group consisting of a poultry species, a porcine species, a caprine species, a bovine species, an ovine species, an equine species, and a companion animal.

3. The method of any one of clauses 1 to 2 wherein the *E. coli* and/or *Clostridium* inhibition prevents *E. coli* and/or *Clostridium* disease in the animal.

4. The method of any one of clauses 1 to 2 wherein the *E. coli* and/or *Clostridium* inhibition reduces *E. coli* and/or *Clostridium* disease in the animal.

5. The method of any one of clauses 1 to 4 wherein the animal is a porcine species and the porcine species is selected from the group consisting of a grow finish pig, a nursery pig, a sow, and a breeding stock pig.

6. The method of any one of clauses 1 to 5 wherein the *Bacillus* strain produces an enzyme selected from the group consisting of an α-galactosidase, a protease, a lipase, an amylase, a xylanase, a cellulase, and combinations thereof.

7. The method of any one of clauses 1 to 6 further comprising the step of administering to the animal another different bacterial strain selected from the group consisting of another *Bacillus* strain, a lactic acid bacterial strain, and combinations thereof.

8. The method of any one of clauses 1 to 7 wherein the strain administered is *Bacillus* strain 2 (NRRL No. B-67709).

9. The method of any one of clauses 1 to 7 wherein the strain administered is *Bacillus* strain 3 (NRRL No. B-67710).

10. The method of any one of clauses 1 to 7 wherein the strain administered is *Bacillus* strain 4 (NRRL No. B-67711).

11. The method of any one of clauses 1 to 7 wherein the strain administered is *Bacillus* strain 5 (NRRL No. B-67712).

12. The method of any one of clauses 1 to 7 wherein the strain administered is *Bacillus* strain 6 (NRRL No. B-67714).

13. The method of any one of clauses 1 to 7 wherein the strain administered is *Bacillus* strain 7 (NRRL No. B-67713).

14. The method of any one of clauses 1 to 13 wherein the *Bacillus* strain is administered in the feed composition at a dose of about $1.0 \times 10^3$ CFU/gram of the feed composition to about $5.0 \times 10^{12}$ CFU/gram of the feed composition.

15. The method of any one of clauses 1 to 13 wherein the *Bacillus* strain is administered in the feed composition at a dose of about $1.0 \times 10^3$ CFU/gram of the feed composition to about $1.0 \times 10^7$ CFU/gram of the feed composition.

16. The method of any one of clauses 1 to 13 wherein the *Bacillus* strain is administered in the feed composition at a dose greater than about $7.0 \times 10^4$ CFU/gram of the feed composition.

17. The method of any one of clauses 1 to 16 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

18. The method of any one of clauses 1 to 17 wherein the animal is a sow and the *Bacillus* strain is administered during lactation.

19. The method of any one of clauses 1 to 17 wherein the animal is a sow and the *Bacillus* strain is administered during gestation.

20. The method of any one of clauses 1 to 19 wherein the feed composition is administered daily to the animal.

21. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

22. The method of any one of clauses 1 to 21 wherein the antibiotic is selected from the group consisting of tylosin, tilmicosin, avilamycin, gentamycin, carbadox, tiamulin, and neomycin.

23. A method of controlling a detrimental effect of *E. coli* and/or *Clostridium*, the method comprising the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* and/or *Clostridium* in the animal.

24. The method of clause 23 wherein the animal is selected from the group consisting of a poultry species, a porcine species, a caprine species, a bovine species, an ovine species, an equine species, and a companion animal.

25. The method of any one of clauses 23 to 24 wherein controlling the detrimental effect of the *E. coli* and/or *Clostridium* is inhibiting *E. coli* and/or *Clostridium* disease in the animal.

26. The method of any one of clauses 23 to 24 wherein controlling the detrimental effect of the *E. coli* and/or *Clostridium* is reducing *E. coli* and/or *Clostridium* disease in the animal.

27. The method of any one of clauses 23 to 26 wherein the animal is a porcine species and the porcine species is selected from the group consisting of a grow finish pig, a nursery pig, a sow, and a breeding stock pig.

28. The method of any one of clauses 23 to 27 wherein the *Bacillus* strain produces an enzyme selected from the group consisting of an α-galactosidase, a protease, a lipase, an amylase, a xylanase, a cellulase, and combinations thereof.

29. The method of any one of clauses 23 to 28 further comprising the step of administering to the animal another different bacterial strain selected from the group consisting of another *Bacillus* strain, a lactic acid bacterial strain, and combinations thereof.

30. The method of any one of clauses 23 to 29 wherein the strain administered is *Bacillus* strain 2 (NRRL No. B-67709).

31. The method of any one of clauses 23 to 29 wherein the strain administered is *Bacillus* strain 3 (NRRL No. B-67710).

32. The method of any one of clauses 23 to 29 wherein the strain administered is *Bacillus* strain 4 (NRRL No. B-67711).

33. The method of any one of clauses 23 to 29 wherein the strain administered is *Bacillus* strain 5 (NRRL No. B-67712).

34. The method of any one of clauses 23 to 29 wherein the strain administered is *Bacillus* strain 6 (NRRL No. B-67714).

35. The method of any one of clauses 23 to 29 wherein the strain administered is *Bacillus* strain 7 (NRRL No. B-67713).

36. The method of any one of clauses 23 to 35 wherein the *Bacillus* strain is administered in the feed composition at a dose of about $1.0 \times 10^3$ CFU/gram of the feed composition to about $5.0 \times 10^{12}$ CFU/gram of the feed composition.

37. The method of any one of clauses 23 to 35 wherein the *Bacillus* strain is administered in the feed composition at a dose of about $1.0 \times 10^3$ CFU/gram of the feed composition to about $1.0 \times 10^7$ CFU/gram of the feed composition.

38. The method of any one of clauses 23 to 35 wherein the *Bacillus* strain is administered in the feed composition at a dose greater than about $7.0 \times 10^4$ CFU/gram of the feed composition.

39. The method of any one of clauses 23 to 38 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

40. The method of any one of clauses 23 to 39 wherein the animal is a sow and the *Bacillus* strain is administered during lactation.

41. The method of any one of clauses 23 to 39 wherein the animal is a sow and the *Bacillus* strain is administered during gestation.

42. The method of any one of clauses 23 to 41 wherein the feed composition is administered daily to the animal.

43. The method of clause 23 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

44. The method of any one of clauses 23 to 43 wherein the antibiotic is selected from the group consisting of tylosin, tilmicosin, avilamycin, gentamycin, carbadox, tiamulin, and neomycin.

45. A method of feeding an animal, the method comprising the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

46. The method of clause 45 wherein the animal is selected from the group consisting of a poultry species, a porcine species, a caprine species, a bovine species, an ovine species, an equine species, and a companion animal.

47. The method of any one of clauses 45 to 46 wherein the animal is a sow.

48. The method of any one of clauses 45 to 46 wherein the animal is a chicken.

49. The method of any one of clauses 45 to 48 wherein the animal is a porcine species and the porcine species is selected from the group consisting of a grow finish pig, a nursery pig, a sow, and a breeding stock pig.

50. The method of any one of clauses 45 to 49 wherein the *Bacillus* strain produces an enzyme selected from the group consisting of an α-galactosidase, a protease, a lipase, an amylase, a xylanase, a cellulase, and combinations thereof.

51. The method of any one of clauses 45 to 50 further comprising the step of administering to the animal another different bacterial strain selected from the group consisting of another *Bacillus* strain, a lactic acid bacterial strain, and combinations thereof.

52. The method of any one of clauses 45 to 51 wherein the strain administered is *Bacillus* strain 2 (NRRL No. B-67709).

53. The method of any one of clauses 45 to 51 wherein the strain administered is *Bacillus* strain 3 (NRRL No. B-67710).

54. The method of any one of clauses 45 to 51 wherein the strain administered is *Bacillus* strain 4 (NRRL No. B-67711).

55. The method of any one of clauses 45 to 51 wherein the strain administered is *Bacillus* strain 5 (NRRL No. B-67712).

56. The method of any one of clauses 45 to 51 wherein the strain administered is *Bacillus* strain 6 (NRRL No. B-67714).

57. The method of any one of clauses 45 to 51 wherein the strain administered is *Bacillus* strain 7 (NRRL No. B-67713).

58. The method of any one of clauses 45 to 57 wherein the *Bacillus* strain is administered in the feed composition at a dose of about $1.0 \times 10^3$ CFU/gram of the feed composition to about $5.0 \times 10^{12}$ CFU/gram of the feed composition.

59. The method of any one of clauses 45 to 57 wherein the *Bacillus* strain is administered in the feed composition at a dose of about $1.0 \times 10^3$ CFU/gram of the feed composition to about $1.0 \times 10^7$ CFU/gram of the feed composition.

60. The method of any one of clauses 45 to 57 wherein the *Bacillus* strain is administered in the feed composition at a dose greater than about $7.0 \times 10^4$ CFU/gram of the feed composition.

61. The method of any one of clauses 45 to 60 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

62. The method of any one of clauses 45 to 61 wherein the animal is a sow and the *Bacillus* strain is administered during lactation.

63. The method of any one of clauses 45 to 61 wherein the animal is a sow and the *Bacillus* strain is administered during gestation.

64. The method of any one of clauses 45 to 63 wherein the feed composition is administered daily to the animal.

65. The method of clause 45 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

66. The method of any one of clauses 45 to 65 further comprising the step of administering an antibiotic wherein the antibiotic is selected from the group consisting of tylosin, tilmicosin, avilamycin, gentamycin, carbadox, tiamulin, and neomycin.

67. The method of any one of clauses 1 to 66 wherein the *Bacillus* strain has an effect selected from the group consisting of maintaining microbial balance in the gut of the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.

68. The method of any one of clauses 1 to 7, 14 to 29, 36 to 51, or 58 to 67 wherein the strain administered is *Bacillus* strain 9 (NRRL No. B-67866).

69. The method of any one of clauses 1 to 7, 14 to 29, 36 to 51, or 58 to 67 wherein the strain administered is *Bacillus* strain 57 (NRRL No. B-67870).

70. The method of any one of clauses 1 to 7, 14 to 29, 36 to 51, or 58 to 67 wherein the strain administered is *Bacillus* strain 71 (NRRL No. B-67867).

71. The method of any one of clauses 1 to 7, 14 to 29, 36 to 51, or 58 to 67 wherein the strain administered is *Bacillus* strain 126 (NRRL No. B-67868).

72. A commercial package comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

73. A feed additive for an animal feed comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

74. An additive for the drinking water of an animal comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

75. An animal feed composition comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

76. The commercial package, feed additive, feed composition, or additive for the drinking water of the animal of any one of clauses 72 to 75 wherein the *Bacillus* strain causes an effect selected from the group consisting of preventing *E. coli* and/or *Clostridium* disease, reducing *E. coli* and/or *Clostridium* disease, maintaining the microbial balance of the animal, and combinations thereof.

77. The commercial package, feed additive, feed composition, or additive for the drinking water of the animal of any one of clauses 72 to 75, wherein the *Bacillus* strain reduces *E. coli* and/or *Clostridium* disease in the animal.

78. The feed additive or additive for the drinking water of the animal of clause 73 or 74 in the form of a concentrate.

79. The feed additive or additive for the drinking water of the animal of clause 73 or 74 in the form of a superconcentrate.

80. The feed additive, feed composition, or additive for the drinking water of the animal of any one of clauses 73 to 79 in dry form.

81. The feed additive, feed composition, or additive for the drinking water of the animal of any one of clauses 73 to 80 in pelleted form.

82. The commercial package, feed additive, feed composition, or additive for the drinking water of the animal of any one of clauses 72 to 79 wherein the strains are in a form selected from the group consisting of a powder, a pellet, a liquid, a liquid drench, a freeze-dried composition, a capsule, a top-dressing, a paste, and a gel.

83. The commercial package, feed additive, additive for the drinking water of the animal, or feed composition of any one of clauses 72 to 82 further comprising a carrier for the *Bacillus* strains.

84. The commercial package, feed additive, additive for the drinking water of the animal, or feed composition of clause 83 wherein the carrier is selected from the group consisting of a bran, rice hulls, a salt, mineral oil, a dextrin (e.g., maltodextrin), whey, sugar, sucrose, limestone, yeast culture, dried starch, sodium silico aluminate, silicon dioxide, polypropylene glycol, polysorbate 80, vegetable oil, and combinations thereof.

85. The commercial package, feed additive, additive for the drinking water of the animal, or feed composition of any one of clauses 72 to 84 in a bag.

86. The commercial package, feed additive, additive for the drinking water of the animal, or feed composition of clause 85 wherein the bag is a plastic bag.

87. The commercial package, feed additive, additive for the drinking water of the animal, or feed composition of any one of clauses 72 to 86 further comprising instructions for use of one or more of the *Bacillus* strains.

88. The commercial package, feed additive, feed composition, or additive for the drinking water of the animal of any one of clauses 72 to 87 in a 20-pound bag.

89. The commercial package, feed additive, feed composition, or additive for the drinking water of the animal of any one of clauses 72 to 87 in a 50-pound bag.

90. The commercial package, feed additive, additive for the drinking water of the animal, or feed composition of any one of clauses 72 to 89 in a container for commercial use.

91. The commercial package, feed additive, additive for the drinking water of the animal, or feed composition of clause 90 wherein the container comprises plastic.

92. The commercial package, feed additive, additive for the drinking water of the animal, or feed composition of clause 90 wherein the container comprises paper.

93. The commercial package, feed additive, additive for the drinking water of the animal, or feed composition of any one of clauses 72 to 92 further comprising a binder.

94. The commercial package, feed additive, additive for the drinking water of the animal, or feed composition of clause 93 wherein the binder is selected from the group consisting of clay, yeast cell wall components, aluminum silicate, and glucan, or combinations thereof.

95. The commercial package, feed additive, additive for the drinking water of the animal, or feed composition of any one of clauses 72 to 94 further comprising an exogenously added nutrient component selected from the group consisting of a vitamin, an antibiotic, an enzyme, a water-soluble or water-insoluble monosaccharide, disaccharide, or polysaccharide, a fat, phosphorous, sodium bicarbonate, limestone, calcium, sodium, sulfur, magnesium, potassium, copper, iron, manganese, zinc, fish oil, raw seed, an antioxidant, and a starch.

96. The commercial package, feed additive, additive for the drinking water of the animal, or feed composition of clause 95 wherein the exogenously added nutrient component is an enzyme and the enzyme is selected from the group consisting of a galactosidase, a protease, a lipase, an amylase, a hemicellulase, an arabinoxylanase, a xylanase, a cellulase, an NSPase, a phytase, and combinations thereof.

97. The commercial package, feed additive, additive for the drinking water of the animal, or feed composition of any one of clauses 72 to 96 wherein the *Bacillus* strains are selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

98. The commercial package, feed additive, additive for the drinking water of the animal, or feed composition of any one of clauses 72 to 96 wherein the *Bacillus* strains are selected from the group consisting of *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

99. The commercial package, feed additive, additive for the drinking water of the animal, or feed composition of any one of clauses 72 to 96 wherein the *Bacillus* strains are selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), and combinations thereof.

In various embodiments, the animal to which a feed additive, a feed composition, or drinking water, and, optionally, an antibiotic, as described herein is administered can be selected from the group consisting of a poultry species, a porcine species, a caprine species, a bovine species, an ovine species, an equine species, and a companion animal.

In the embodiment where the animal is a companion animal, the companion animal can be, for example, a canine species or a feline species. In the embodiment where the animal is a porcine species, the porcine species can be selected from the group consisting of a grow finish pig, a nursery pig, a sow, and a breeding stock pig. In various exemplary embodiments, the animal can be selected from the group consisting of a chicken (e.g., a broiler or a layer), a pig, a horse, a pony, a cow, a turkey, a goat, a sheep, a quail, a pheasant, an ostrich, a duck, a fish (e.g., a tilapia, a catfish, a flounder, or a salmon), a crustacean (e.g., a shrimp or a crab), and combinations thereof. In another embodiment, the feed additive, feed composition, or drinking water, and, optionally, the antibiotic, as described herein is administered to an animal and the animal is a human.

In various embodiments of the methods or compositions described herein, the *Bacillus* strain and the antibiotic can have an effect selected from the group consisting of maintaining microbial balance in the gut of the animal, preventing or reducing *E. coli* and/or *Clostridium* disease in the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal. In any of the embodiments described herein, the *Bacillus* strain can be a *Bacillus subtilis* strain (e.g., strains 2, 3, 6, 7, 9, 57, 71, and/or 126) or a *Bacillus licheniformis* strain (e.g., strains 4 and 5).

In any embodiments described herein, the *Bacillus* strains can be administered alone or in any combination, with or without antibiotics, or can be in the form of any composition described herein. In one embodiment, the strain or strains are administered with an antibiotic in the same or separate compositions. The *Bacillus* strains described herein, with or without antibiotics, can also be used in combination with other different microbial strains, including other *Bacillus* strains or *Lactobacillus* strains.

In one embodiment of the invention, an effective amount of the *Bacillus* strain can be administered to inhibit *E. coli* and/or *Clostridium* in the animal. As used herein, "inhibit *E. coli* and/or *Clostridium*" can mean reducing *E. coli* and/or *Clostridium* disease, preventing *E. coli* and/or *Clostridium* disease, maintaining the normal microbial balance in the animal, reducing the number of detrimental *E. coli* and/or *Clostridium* organisms in the animal, reducing the activity of *E. coli* and/or *Clostridium* in the animal, or reducing the symptoms of *E. coli* and/or *Clostridium* disease in the animal, or combinations thereof. By "effective amount" is meant an amount of the *Bacillus* strain (e.g., strain 2, 3, 4, 5, 6, 7, 9, 57, 71, or 126) capable of *E. coli* and/or *Clostridium* inhibition or capable of controlling a detrimental effect of *E. coli* and/or *Clostridium*, as described below, by any mechanism.

In embodiments described herein wherein the compositions of the present invention comprising *Bacillus* strains 2, 3, 4, 5, 6, 7, 9, 57, 71, and/or 126, or strains having their identifying characteristics, with or without antibiotics are administered to an animal, the compositions are preferably administered to animals orally in a feed composition or in drinking water, but any other effective method of administration known to those skilled in the art may be utilized such as in a paste, a gel, a liquid drench, a liquid, a top dress, a powder, or a capsule. In one illustrative embodiment, the *Bacillus* strains 2, 3, 4, 5, 6, 7, 9, 57, 71, and/or 126, or strains having their identifying characteristics, and/or the antibiotics, are provided in the form of an additive for addition to the drinking water of an animal.

In another illustrative embodiment, the *Bacillus* strains 2, 3, 4, 5, 6, 7, 9, 57, 71, and/or 126, or strains having their identifying characteristics, and/or the antibiotics, are provided in the form of a feed additive for addition to a feed composition. The feed composition may contain *Bacillus* strain 2, 3, 4, 5, 6, 7, 9, 57, 71, and/or 126, or strains having their identifying characteristics, in a mixture with an animal feed blend, including any art-recognized animal feed blend or any animal feed blend described herein. As used herein, "feed composition" or "animal feed composition" means a feed composition comprising *Bacillus* strain 2, 3, 4, 5, 6, 7, 9, 57, 71, and/or 126, or strains having their identifying characteristics, and/or, optionally, the antibiotics in a mixture with an animal feed blend, and, optionally any other components that could be used in a feed composition, including other bacterial strains, such as other different *Bacillus* strains or *Lactobacillus* strains. In one embodiment, the feed composition may be in the form of a ground meal.

Any animal feed blend, including those known in the art and those described herein, may be used in accordance with the methods and compositions described in this patent application, such as rapeseed meal, cottonseed meal, soybean meal, cornmeal, barley, wheat, silage, and haylage. In various embodiments, the animal feed blend can be supplemented with *Bacillus* strain 2, 3, 4, 5, 6, 7, 9, 57, 71, and/or 126, or strains having their identifying characteristics, and/or, optionally, the antibiotics, but other ingredients may optionally be added to the animal feed blend, including other different bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In various embodiments, the antibiotic for use in the methods and compositions described herein is selected from the group consisting of ampicillin, chloramphenicol, ciprofloxacin, clindamycin, tetracycline, chlortetracycline, Denagard® (i.e., tiamulin), BMD® (i.e., bacitracin methylene disalicylate), carbadox (i.e., Mecadox®), Stafac® (i.e., virginiamycin), erythromycin, levofloxacin, trimethoprim/sulfamethoxazole, trimethoprim, daptomycin, rifampicin, Tylan® (i.e., tylosin), Pulmotil® (i.e., tilmicosin), vancomycin, avilamycin (Kavault®), gentamycin, and neomycin, and combinations thereof. In one illustrative embodiment, the antibiotic is selected from the group consisting of tylosin, tilmicosin, avilamycin, gentamycin, carbadox, tiamulin, and neomycin.

In various embodiments where gentamycin is used, the dosage can be based on the Agrilabs® Gen-Gard® soluble powder specification for the treatment of colibacillosis (bacterial enteritis) and swine dysentery in weaned pigs. In various embodiments where neomycin is used, the dosage can be based on Agrilabs® Neomycin Sulfate oral solution specification for the individual treatment of colibacillosis (bacterial enteritis) caused by *E. coli*. In various embodiments where Kavault® is used, the dosage can be based on the Elanco specification for the treatment of *E. coli* related diarrhea in weaned pigs. In various embodiments where tylosin is used, the dosage can be based on the Elanco® specification for the treatment of swine dysentery and porcine proliferative enteropathies. In various embodiments where Pulmotil™ is used, the dosage can be based on the Elanco® specification for the control of swine respiratory disease associated with *A. pleuropneumoniae* and *P. multocida*.

In various embodiments, the dosage of the antibiotic can be from about 0.1 mg/pound of feed to about 1000 mg/pound of feed, about 0.1 mg/pound of feed to about 900 mg/pound of feed, about 0.1 mg/pound of feed to about 800 mg/pound of feed, about 0.1 mg/pound of feed to about 700 mg/pound of feed, about 0.1 mg/pound of feed to about 600 mg/pound of feed, about 0.1 mg/pound of feed to about 500 mg/pound of feed, about 0.1 mg/pound of feed to about 400 mg/pound of feed, about 0.1 mg/pound of feed to about 300 mg/pound of feed, about 0.1 mg/pound of feed to about 200 mg/pound of feed, about 0.1 mg/pound of feed to about 100 mg/pound of feed, about 0.1 mg/pound of feed to about 90 mg/pound of feed, about 0.1 mg/pound of feed to about 80 mg/pound of feed, about 0.1 mg/pound of feed to about 70 mg/pound of feed, about 0.1 mg/pound of feed to about 60 mg/pound of feed, about 0.1 mg/pound of feed to about 50 mg/pound of feed, about 0.1 mg/pound of feed to about 40 mg/pound of feed, about 0.1 mg/pound of feed to about 30 mg/pound of feed, about 0.1 mg/pound of feed to about 20 mg/pound of feed, about 0.1 mg/pound of feed to about 10 mg/pound of feed, about 0.1 mg/pound of feed to about 9 mg/pound of feed, about 0.1 mg/pound of feed to about 8 mg/pound of feed, about 0.1 mg/pound of feed to about 7 mg/pound of feed, about 0.1 mg/pound of feed to about 6 mg/pound of feed, about 0.1 mg/pound of feed to about 5 mg/pound of feed, about 0.1 mg/pound of feed to about 4 mg/pound of feed, about 0.1 mg/pound of feed to about 3 mg/pound of feed, about 0.1 mg/pound of feed to about 2 mg/pound of feed, about 0.1 mg/pound of feed to about 1 mg/pound of feed, about 0.1 mg/pound of feed to about 0.5 mg/pound of feed, about 0.1 mg/pound of feed to about 0.3 mg/pound of feed, about 0.5 mg/pound of feed to about 1 mg/pound of feed, about 1 mg/ml to about 1000 mg/ml of drinking water, about 1 mg/ml to about 900 mg/ml of drinking water, about 1 mg/ml to about 800 mg/ml of drinking water, about 1 mg/ml to about 700 mg/ml of drinking water, about 1 mg/ml to about 600 mg/ml of drinking water, about 1 mg/ml to about 500 mg/ml of drinking water, about 1 mg/ml to about 400 mg/ml of drinking water, about 1 mg/ml to about 300 mg/ml of drinking water, about 1 mg/ml to about 200 mg/ml of drinking water, about 1 mg/ml to about 100 mg/ml of drinking water, about 50 mg/ml to about 100 mg/ml of drinking water, about 50 mg/ml to about 90 mg/ml of drinking water, about 50 mg/ml to about 80 mg/ml of drinking water, about 50 mg/ml to about 70 mg/ml of drinking water, about 50 mg/ml to about 60 mg/ml of drinking water, about 1000 ppm, about 900 ppm, about 800 ppm, about 700 ppm, about 600 ppm, about 500 ppm, about 400 ppm, about 300 ppm, about 200 ppm, about 100 ppm, about 90 ppm, about 80 ppm, about 70 ppm, about 60 ppm, about 50 ppm, about 40 ppm, about 30 ppm, about 20 ppm, or about 10 ppm.

In another illustrative embodiment, one or more enzymes may be added to the animal feed blend or to the feed composition or feed additive or the bacterial strain. In various embodiments, the enzymes that may be added include a galactosidase, a phytase, a protease, a lipase, an amylase, a hemicellulase, an arabinoxylanase, a xylanase, a cellulase, an NSPase, combinations thereof, and any other enzyme that improves the effectiveness of the feed composition or feed additive for *E. coli* and/or *Clostridium* inhibition or controlling a detrimental effect of *E. coli* and/or *Clostridium*. In yet another embodiment, yeast, fungi (e.g., *Aspergillus* or *Trichoderma*), or micronutrients may be added to the animal feed, feed composition, or feed additive, or the bacterial strain. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus* strain 2, 3, 4, 5, 6, 7, 9, 57, 71, and/or 126, or strains having their identifying characteristics), or any other different bacterial strains added in addition to *Bacillus* strain 2, 3, 4, 5, 6, 7, 9, 57, 71, and/or 126, or strains having their identifying characteristics, can be administered in the feed composition at a dose of about $1.0 \times 10^3$ CFU/gram of the feed composition to about $5.0 \times 10^{12}$ CFU/gram of the feed composition or at a dose of about $1.0 \times 10^3$ CFU/gram of the feed composition to about $1.0 \times 10^7$ CFU/gram of the feed composition. In other embodiments, the *Bacillus* strain (e.g., *Bacillus* strain 2, 3, 4, 5, 6, 7, 9, 57, 71, and/or 126, or strains having their identifying characteristics) is administered in the feed composition at a dose greater than about $1.0 \times 10^3$ CFU/gram of the feed composition, at a dose greater than about $1.1 \times 10^3$ CFU/gram of the feed composition, at a dose greater than about $1.25 \times 10^3$ CFU/gram of the feed composition, at a dose greater than about $1.5 \times 10^3$ CFU/gram of the feed composition, at a dose greater than about $1.75 \times 10^3$ CFU/gram of the feed composition, at a dose greater than about $1.0 \times 10^4$ CFU/gram of the feed composition, at a dose greater than about $2.0 \times 10^4$ CFU/gram of the feed composition, at a dose greater than about $3.0 \times 10^4$ CFU/gram of the feed composition, at a dose greater than about $4.0 \times 10^4$ CFU/gram of the feed composition, at a dose greater than about $5.0 \times 10^4$ CFU/gram of the feed composition, at a dose greater than about $6.0 \times 10^4$ CFU/gram of the feed composition, at a dose greater than about $7.0 \times 10^4$ CFU/gram of the feed composition, at a dose greater than about $8.0 \times 10^4$ CFU/gram of the feed composition, at a dose greater than about $1.0 \times 10^5$ CFU/gram of the feed composition, at a dose greater than about $1.0 \times 10^6$ CFU/gram of the feed composition, at a dose greater than about $1.0 \times 10^7$ CFU/gram of the feed composition, at a dose greater than about $1.0 \times 10^8$ CFU/gram of the feed composition, at a dose greater than about $1.0 \times 10^9$ CFU/gram of the feed composition, at a dose greater than about $1.0 \times 10^{10}$ CFU/gram of the feed composition, at a dose greater than about $1.0 \times 10^{11}$ CFU/gram of the feed composition, or at a dose greater than about $1.0 \times 10^{12}$ CFU/gram of the feed composition. In another embodiment, the *Bacillus* strain (e.g., *Bacillus* strain 2, 3, 4, 5, 6, 7, 9, 57, 71, and/or 126, or strains having their identifying characteristics), or any other different bacterial strains added in addition to *Bacillus* strain 2, 3, 4, 5, 6, 7, 9, 57, 71, and/or 126, or strains having their identifying characteristics, can be administered in the feed composition at a dose of about $1.0 \times 10^2$ CFU/gram of the feed composition to about $5.0 \times 10^{12}$ CFU/gram of the feed composition or at a dose of about $1.0 \times 10^2$ CFU/gram of the feed composition to about $1.0 \times 10^7$ CFU/gram of the feed composition, or at a dose greater than about $1.0 \times 10^2$ CFU/gram of the feed composition. In another embodiment, any of the dosages described herein can be in CFU/ml of drinking water in embodiments where the strains are administered in the drinking water of the animal.

In various embodiments, the *Bacillus* strain (e.g., *Bacillus* strain 2, 3, 4, 5, 6, 7, 9, 57, 71, and/or 126, or strains having their identifying characteristics) for use in accordance with the methods or compositions described herein can be selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof. *Bacillus* strains 2, 3, 4, 5, 6, and 7 were deposited on Nov. 29, 2018 at the Agricultural Research Service Culture Collection (NRRL), National Center for Agricultural Utilization Research, Agricultural Research Service, USDA, 1815 North University Street, Peoria, Illinois 61604-3999, and were given accession numbers NRRL No. B-67709, NRRL No. B-67710, NRRL No., B-67711, NRRL No. B-67712, NRRL No. B-67714, and NRRL No. B-67713, respectively, respectively. The deposits were made under the provisions of the Budapest Treaty on the International Recognition of the Deposit of Microorganisms for the Purposes of Patent Procedure. NRRL No. B-67709, NRRL No. B-67710, NRRL No., B-67711, NRRL No. B-67712, NRRL No. B-67714, and NRRL No. B-67713, are equivalent to *Bacillus* strains 2, 3, 4, 5, 6, and 7, respectively, as referred to in the application.

*Bacillus* strains 9, 57, 71, and 126 were deposited on Oct. 10, 2019 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67866, B-67870, B-67867, and B-67868, respectively. The deposits were made under the provisions of the Budapest Treaty on the International Recognition of the Deposit of Microorganisms for the Purposes of Patent Procedure. NRRL No. B-67866, NRRL No. B-67870, NRRL No., B-67867, and NRRL No. B-67868, are equivalent to *Bacillus* strains 9, 57, 71, and 126, respectively, as referred to in the application. The deposit certificates refer to the strains as MDG9, MDG57, MDG71, and MDG126, respectively.

In one aspect, any of these strains can be administered alone or in combination in the form of a feed composition (e.g., a complete feed comprising an animal feed blend) or drinking water for an animal. In one embodiment, multiple strains are administered in combination in a single composition. In another embodiment, multiple strains are administered in combination in separate compositions. In yet another embodiment, any of these strains, or combinations thereof, is administered in combination with an antibiotic, as described herein in the same or separate compositions.

In another embodiment, one or more of the *Bacillus* strains described in the preceding paragraphs (e.g., *Bacillus* strain 2, 3, 4, 5, 6, 7, 9, 57, 71, and/or 126, or strains having their identifying characteristics) can be administered to the animal along with another different bacterial strain selected from the group consisting of another *Bacillus* strain, a lactic acid bacterial strain, and combinations thereof. In yet another embodiment, one or more of the *Bacillus* strains described in the preceding paragraphs (e.g., *Bacillus* strain 2, 3, 4, 5, 6, 7, 9, 57, 71, and/or 126, or strains having their identifying characteristics) can be administered to the animal along with any other bacterial strain effective to inhibit or control detrimental effects of *E. coli* and/or *Clostridium* in the animal.

As used herein "a strain having all of the identifying characteristics of" *Bacillus* strain 2, 3, 4, 5, 6, 7, 9, 57, 71, and/or 126 can be a mutant strain having all of the identifying characteristics of *Bacillus* strain 2, 3, 4, 5, 6, 7, 9, 57, 71, or 126 (e.g., a DNA fingerprint based on DNA analysis that corresponds to the DNA fingerprint of *Bacillus* strain 2, 3, 4, 5, 6, 7, 9, 57, 71, or 126, enzyme activities that correspond to *Bacillus* strain 2, 3, 4, 5, 6, 7, 9, 57, 71, or 126, antimicrobial activity that corresponds to *Bacillus* strain 2, 3, 4, 5, 6, 7, 9, 57, 71, or 126, antibiotic sensitivity and tolerance profiles that correspond to *Bacillus* strain 2, 3, 4, 5, 6, 7, 9, 57, 71, or 126, or combinations of these identifying characteristics). In alternate embodiments, the mutation can be a natural mutation, or a genetically engineered mutation. In another embodiment, "a strain having all of the identifying characteristics of" *Bacillus* strain 2, 3, 4, 5, 6, 7, 9, 57, 71, or 126 can be a strain, for example, produced by isolating one or more plasmids from *Bacillus* strain 2, 3, 4, 5, 6, 7, 9, 57, 71, or 126, and introducing the one or more plasmids into another bacterium, such as another *Bacillus* strain, as long as the one or more plasmids contain DNA that provides the identifying characteristics of *Bacillus* strain 2, 3, 4, 5, 6, 7, 9, 57, 71, or 126 (e.g., a DNA fingerprint based on DNA analysis that corresponds to the DNA fingerprint of *Bacillus* strain 2, 3, 4, 5, 6, 7, 9, 57, 71, or 126).

The feed composition or drinking water comprising *Bacillus* strain 2, 3, 4, 5, 6, 7, 9, 57, 71, and/or 126, or strains with their identifying characteristics, and the antibiotics described herein, may be administered to the animal for any time period that is effective to inhibit *E. coli* and/or *Clostridium* or control a detrimental effect of *E. coli* and/or *Clostridium*, or combinations thereof. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective to inhibit *E. coli* and/or *Clostridium* or control a detrimental effect of *E. coli* and/or *Clostridium*, or combinations thereof, may be used.

In embodiments involving "controlling a detrimental effect of *E. coli* and/or *Clostridium*" controlling a detrimental effect can mean reducing *E. coli* and/or *Clostridium* disease, preventing *E. coli* and/or *Clostridium* disease, maintaining the normal microbial balance in the animal, reducing the number of detrimental *E. coli* and/or *Clostridium* in the animal, reducing the activity of *E. coli* and/or *Clostridium* in the animal, or reducing the symptoms of *E. coli* and/or *Clostridium* disease in the animal, or combinations thereof. By "effective amount" is meant an amount of the *Bacillus* strain (e.g., *Bacillus* strain 2, 3, 4, 5, 6, 7, 9, 57, 71, and/or 126) capable of controlling a detrimental effect of *E. coli* and/or *Clostridium* as described herein, by any mechanism.

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain 2, 3, 4, 5, 6, 7, 9, 57, 71, and/or 126, or strains with their identifying characteristics, described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiment where *Bacillus* strain 2, 3, 4, 5, 6, 7, 9, 57, 71, and/or 126, or strains with their identifying characteristics, are in the form of an additive for the drinking water of the animal, the *Bacillus* strain 2, 3, 4, 5, 6, 7, 9, 57, 71, and/or 126, or strains with their identifying characteristics, can be in the form of, for example, a powder, a liquid, or pellets, and can be mixed with the drinking water using any suitable method known in the art to achieve any of the doses of *Bacillus* strain 2, 3, 4, 5, 6, 7, 9, 57, 71, and/or 126, or strains with their identifying characteristics, described herein, for administration to the animal in the drinking water of the animal. *Bacillus* strain 2, 3, 4, 5, 6, 7, 9, 57, 71, and/or 126, or strains with their identifying characteristics, can also be fed directly to the animal orally (i.e., by oral insertion) in the form of a powder, a freeze-dried composition, a gel, a top-dressing, a liquid, a capsule, a paste, a liquid drench, or a pellet. Any of these embodiments can also be applied to mixing and administration of the antibiotics described herein.

In additional embodiments of the invention, compositions are provided comprising *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In one embodiment, a commercial package is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In another embodiment, a feed additive for an animal feed is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In yet another embodiment, an additive for the drinking water of an animal is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In yet another illustrative aspect of the invention, an animal feed composition is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In one illustrative aspect, the strains for addition to the commercial package, feed additive, additive for the drinking water of the animal, or the feed composition can be in the form of a concentrate (e.g., about $1 \times 10^8$ to about $5 \times 10^9$ CFU/g) or a superconcentrate (e.g., about $1 \times 10^{10}$ to about $5 \times 10^{12}$ CFU/g). In another embodiment, the strains for addition to the commercial package, feed additive, feed composition, or additive for the drinking water of the animal can be in a dry form (e.g., a powder), a pelleted form, a liquid form, a liquid drench, a powder, a freeze-dried composition, in the form of a top-dressing, a paste, or in the form of a gel, or any other suitable form.

In another illustrative embodiment, the strain or strains in the commercial package, the feed additive, additive for the drinking water of the animal, or feed composition can further comprise a carrier for the *Bacillus* strain or strains. The carrier can be selected from the group consisting of a bran, rice hulls, a salt, mineral oil, a dextrin (e.g., maltodextrin), whey, sugar, sucrose, limestone, yeast culture, dried starch, sodium silico aluminate, silicon dioxide, polypropylene glycol, polysorbate 80, vegetable oil, and combinations thereof. In another embodiment, the carrier can be any suitable carrier known in the art for a direct-fed microbial. The carrier is exogenously added to the bacterial strain (i.e., not naturally present or not present in nature with the bacterial strain). In another embodiment, the feed additive, additive for the drinking water of the animal, or feed composition can further comprise a binder such as clay, yeast cell wall components, aluminum silicate, or glucan. In another embodiment, the commercial package, feed additive, additive for the drinking water of the animal, or feed composition can further comprise inorganic/organic binders, essential oils, and/or organic acids. The binder is exogenously added to the bacterial strain (i.e., not naturally present or not present in nature with the bacterial strain).

In yet other embodiments, the commercial package, feed additive, additive for the drinking water of the animal, or feed composition comprising *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, is in a container for commercial use.

In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package, feed additive, additive for the drinking water of the animal, or feed composition comprising *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 6 (NRRL No. B-67714), a strain having all of the identifying characteristics of *Bacillus* strain 6 (NRRL No. B-67714), *Bacillus* strain 7 (NRRL No. B-67713), a strain having all of the identifying characteristics of *Bacillus* strain 7 (NRRL No. B-67713), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, can comprise plastic, metal, foil, paper, fiber, or cardboard (e.g., a plastic pail, a paper bag, a foil bag, a fiber drum, etc.). The commercial package, feed additive, additive for the drinking water of the animal, or feed composition can further comprise instructions for use of one or more of the *Bacillus* strains.

In one aspect, the commercial package, feed additive, additive for the drinking water of the animal, or feed composition described herein can further comprise an exogenously added nutrient component (i.e., a nutrient component not present with the bacterial strain in nature) selected from the group consisting of a vitamin, an antibiotic, an enzyme, a water-soluble or water-insoluble monosaccharide, disaccharide, or polysaccharide, a fat, phosphorous, sodium bicarbonate, limestone, calcium, sodium, sulfur, magnesium, potassium, copper, iron, manganese, zinc, fish oil, raw seed, an antioxidant, and a starch.

In one embodiment, the exogenously added nutrient component is an enzyme and the enzyme is selected from the group consisting of a galactosidase, a protease, a lipase, an amylase, a hemicellulase, an arabinoxylanase, a xylanase, a cellulase, an NSPase, a phytase, and combinations thereof.

In one embodiment, any of the compositions described herein can be a dietary nutrient composition (e.g., a probiotic composition).

In one aspect, the commercial package, feed additive, additive for the drinking water of the animal, or feed composition described herein can contain *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In another embodiment, the commercial package, feed additive, additive for the drinking water of the animal, or feed composition can contain *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In some embodiments of the methods and compositions described herein, synergism occurs between the *Bacillus* strains and the antibiotics.

The following examples are for illustrative purposes only. The examples are non-limiting, and are not intended to limit the invention in any way.

Example 1

Bacillus Testing on Kavault (32), Pulmotil (64), and Tylan (68) Resistant *E. coli*

Utilizing a broth AST method, eight *Bacillus* strains were tested against 32 Kavault-resistant *E. coli*, 68 Tylan-resistant *E. coli*, and 64 Pulmotil-resistant *E. coli*. Six *Bacillus* strains were observed to have been most effective against Pulmotil, Tylan, and Kavault resistant *E. coli*. *Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 6 (NRRL No. B-67714), and *Bacillus* strain 7 (NRRL No. B-67713) consistently improved and effectively inhibited (>50% inhibition) antibiotic resistant pathogens when the same concentration of antibiotic was administered in conjunction with *Bacillus* supernatant.

Example 2

Tilmicosin Resistant *E. coli*

Of the 64 Tilmicosin resistant *E. coli*, when combined with antibiotics, *Bacillus* strains 2, 3, and 6 effectively inhibited 64/64 isolates. Of the 64 Tilmicosin resistant *E. coli*, when combined with antibiotics, *Bacillus* strain 5 effectively inhibited 63/64 isolates. Of the 64 Tilmicosin resistant *E. coli*, when combined with antibiotics, *Bacillus* strains 4 and 7 effectively inhibited 62-64 isolates.

Example 3

Tylosin Resistant *E. coli*

Of the 68 Tylosin resistant *E. coli*, when combined with antibiotics, *Bacillus* strains 2, 3, & 4 improved inhibition in 68/68 isolates. Of the 68 Tylosin resistant *E. coli*, when combined with antibiotics, *Bacillus* strains 5 & 6 improved inhibition in 66/68 isolates. Of the 68 Tylosin resistant *E. coli*, when combined with antibiotics, *Bacillus* strain 7 improved inhibition in 65/68 isolates.

Example 4

Avilamycin Resistant *E. coli*

Of the 32 Avilamycin resistant *E. coli*, when combined with antibiotics, *Bacillus* strains 2 & 3 improved inhibition in 32/32 isolates. Of the 32 Avilamycin resistant *E. coli*, when combined with antibiotics, *Bacillus* strains 5 & 7 improved inhibition in 31/32 isolates. Of the 32 Avilamycin resistant *E. coli*, when combined with antibiotics, *Bacillus* strain 6 improved inhibition in 30/32 isolates. Of the 32 Avilamycin resistant *E. coli*, combined with antibiotics, *Bacillus* strain 4 improved inhibition in 29/32 isolates.

Example 5

*Bacillus* Testing on Gentamicin & Neomycin Resistant *E. coli* (46) & *C. perfringens* (66) Isolates Utilizing a broth AST method, eight *Bacillus* strains were tested against 46 Gentamicin & Neomycin-resistant *E. coli* and 66 Gentamicin & Neomycin-resistant *C. perfringens*. Six *Bacillus* strains were observed to have been most effective. *Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 6 (NRRL No. B-67714), and *Bacillus* strain 7 (NRRL No. B-67713) consistently improved and effectively inhibited (>50% inhibition) antibiotic resistant pathogens when the same concentration of antibiotic was administered in conjunction with *Bacillus* supernatant.

Example 6

Gentamicin & Neomycin Resistant *E. coli*

Of the 50 Gentamicin and Neomycin resistant *E. coli*, when combined with antibiotics, *Bacillus* strains 2-7 each effectively inhibited 50/50 isolates.

Example 7

Gentamicin & Neomycin Resistant *C. perfringens*

Of the 66 Gentamicin and Neomycin resistant *C. perfringens*, when combined with antibiotics, *Bacillus* strains 3, 6, and 7 effectively inhibited 66/66 isolates. Of the 66 Gentamicin and Neomycin resistant *C. perfringens*, when combined with antibiotics *Bacillus* strain 2 effectively inhibited 63/66 isolates. Of the 66 Gentamicin and Neomycin resistant *C. perfringens*, when combined with antibiotics *Bacillus* strains 4 and 5 effectively inhibited 60/66 isolates.

Example 8

*Bacillus* Testing on Mecadox™ (31) Resistant *E. coli*

Utilizing a broth AST method, eight *Bacillus* strains were tested against 31 Mecadox™-resistant *E. coli*. All eight *Bacillus* strains were observed to be more effective at inhibiting the growth of these resistant *E. coli* than Mecadox™ (i.e., carabadox) was capable of alone.

*Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 9 (NRRL No. B-67866), *Bacillus* strain 57 (NRRL No. B-67870), *Bacillus* strain 71 (NRRL No. B-67867), and *Bacillus* strain 126 (NRRL No. B-67868) effectively inhibited (>50% inhibition) Mecadox™ resistant pathogens when the same concentration of the antibiotic was administered in conjunction with the *Bacillus* supernatant. See FIGS. 8A and B and FIG. 9 for examples.

Of the 31 Mecadox™ resistant *E. coli*: when compared to Mecadox™ alone, *Bacillus* strains 2, 3, 4, 5, and 57 superiorly inhibited 31/31 isolates. When compared to Mecadox™ alone, *Bacillus* strains 9, 71, and 126 superiorly inhibited 30/31 isolates.

The goal of this project was to identify *Bacillus* strains that exhibit inhibition potential of target pathogens in combination with antibiotics. Synergy can be defined as a resulting higher percent inhibition of antibiotic-resistant pathogens when *Bacillus* supernatants are combined with antibiotics than when the supernatant and antibiotic are tested separately against the same isolates. Eight *Bacillus* strains yielded consistent strong inhibition activity against Mecadox™-resistant *E. coli* that were tested. These eight *Bacillus* strains (*Bacillus* strains 2, 3, 4, 5, 9, 57, 71, and 126), are identified as strains (NRRL No. B-67709), (NRRL No. B-67710), (NRRL No. B-67711), (NRRL No. B-67712), (NRRL No. B-67866), (NRRL No. B-67870), (NRRL No. B-67867), and (NRRL No. B-67868), respectively.

Example 9

*Bacillus*-Antibiotic Interactions Against Antibiotic-Resistant Gut Pathogens

*Bacillus* strains 9, 57, 71 and 126 consistently improved and effectively inhibited (>50% inhibition) antibiotic resistant pathogens when the same concentration of antibiotic was administered in conjunction with the *Bacillus* supernatant.

Figure 10:
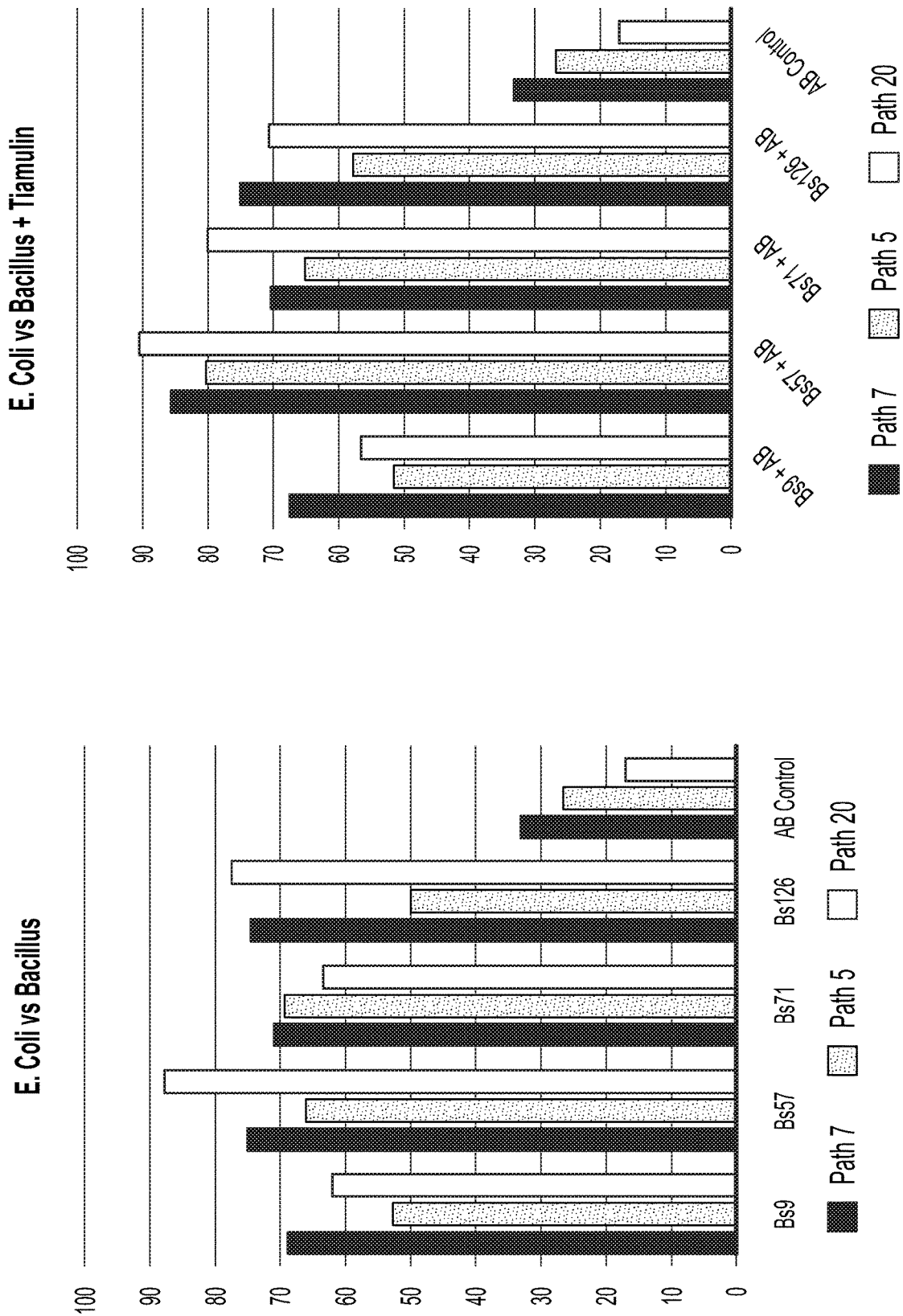
FIG. 10 shows percent inhibition values from 3 of 23 *E. coli* showing an improved inhibition response with *Bacillus* supernatant and Tiamulin compared to Tiamulin alone.

Of the 23 Denagard™ (i.e., tiamulin) resistant *E. coli*: when combined with antibiotics, *Bacillus* strain 9 improved inhibition in 22/23 isolates. When combined with antibiotics, *Bacillus* strain 57 improved inhibition in 21/23 isolates. When combined with antibiotics *Bacillus* strain 71 improved inhibition in 20/23 isolates. When combined with antibiotics *Bacillus* strain 126 improved inhibition in 21/23 isolates. In combination, *Bacillus* strains 9, 57, 71, and 126 effectively inhibited all 23 Denagard™ resistant isolates (see FIG. 10 for an example).

The goal of this project was to identify *Bacillus* strains that exhibit strong inhibition potential of target pathogens in combination with antibiotics. Synergy can be defined as a resulting higher percent inhibition of antibiotic-resistant pathogens when *Bacillus* supernatants are combined with antibiotics than when the supernatant and antibiotic are tested separately against the same isolates. Ten *Bacillus* strains yielded consistent strong inhibition activity against Pulmotil, Tylan, Denagard™, and Kavault-resistant *E. coli* that were tested. These ten *Bacillus* strains (*Bacillus* strains 2, 3, 4, 5, 6, 7, 9, 57, 71, and 126), are identified as strains (NRRL No. B-67709), (NRRL No. B-67710), (NRRL No. B-67711), (NRRL No. B-67712), (NRRL No. B-67714), (NRRL No. B-67713), (NRRL No. B-67866), (NRRL No. B-67870), (NRRL No. B-67867), and (NRRL No. B-67868), respectively.

Example 10

RAPD-PCR DNA Profiles

Figure 7:
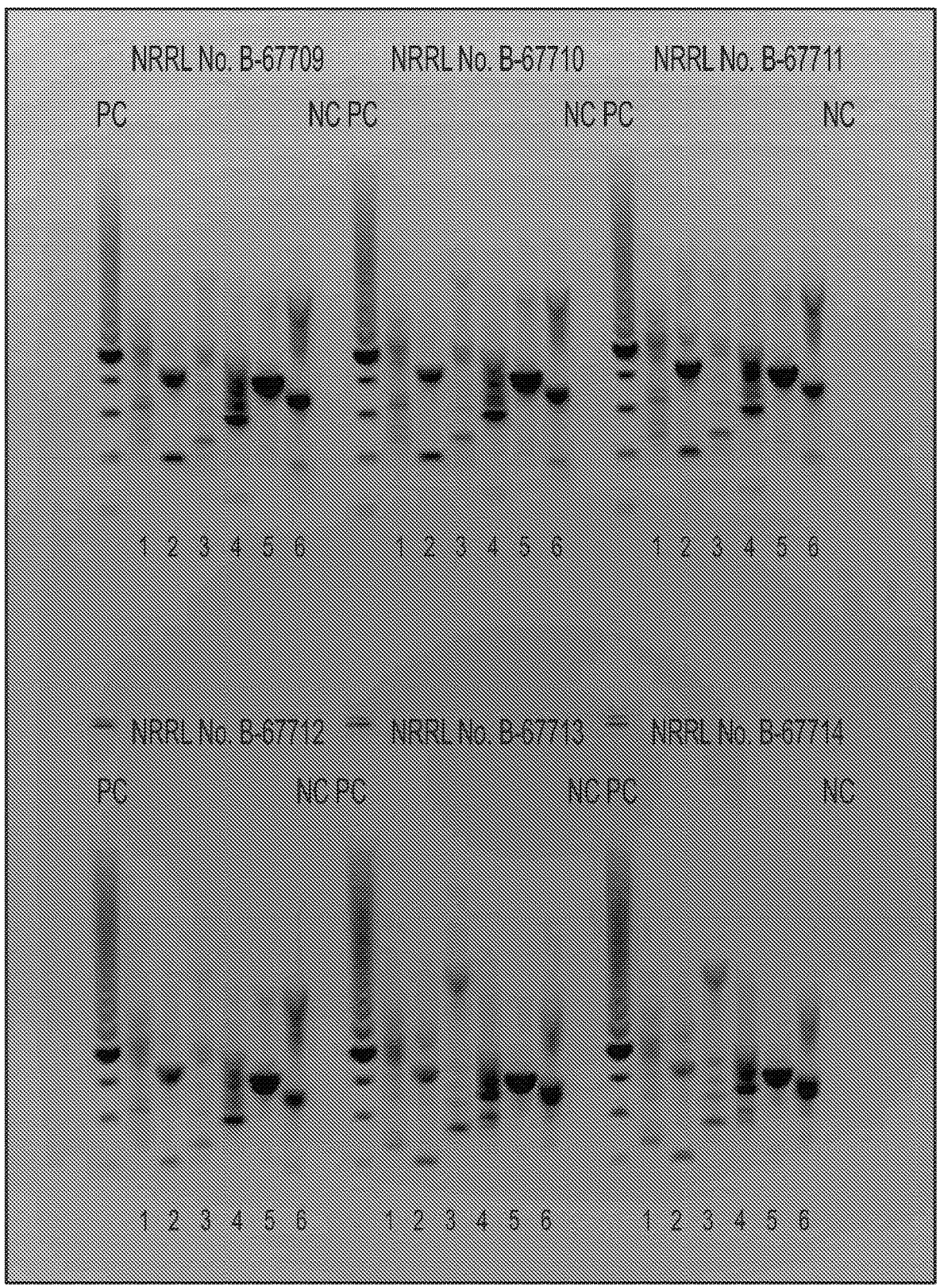
FIG. 7 is a photograph displaying RAPD PCR profiles for *Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 6 (NRRL No. B-67714), and *Bacillus* strain 7 (NRRL No. B-67713).
Figure 8:
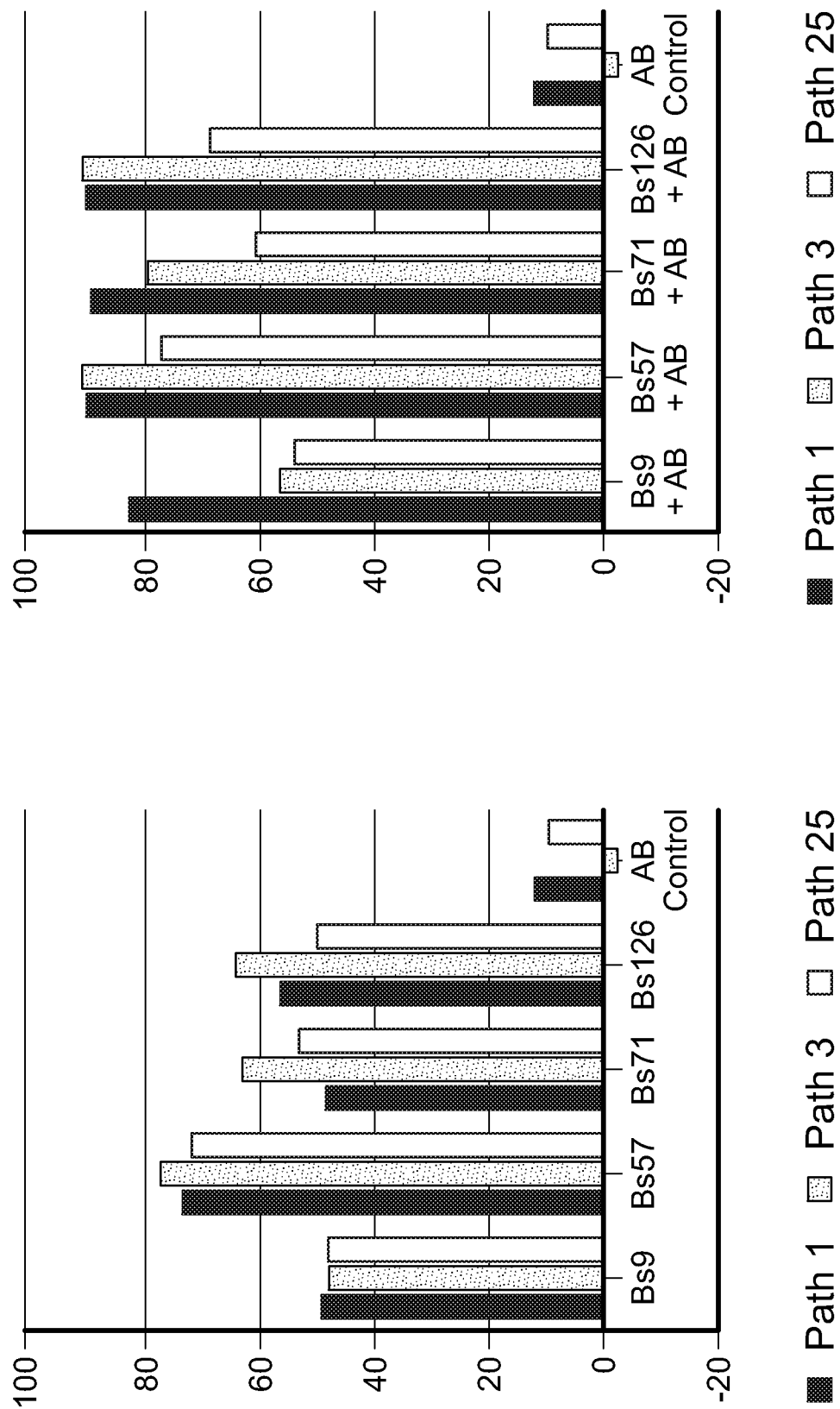
FIGS. 8A-B show percent inhibition values from 3 of 31 *E. coli* isolates showing an improved inhibition response when *Bacillus* supernatant and Carbadox are combined.
Figure 11:
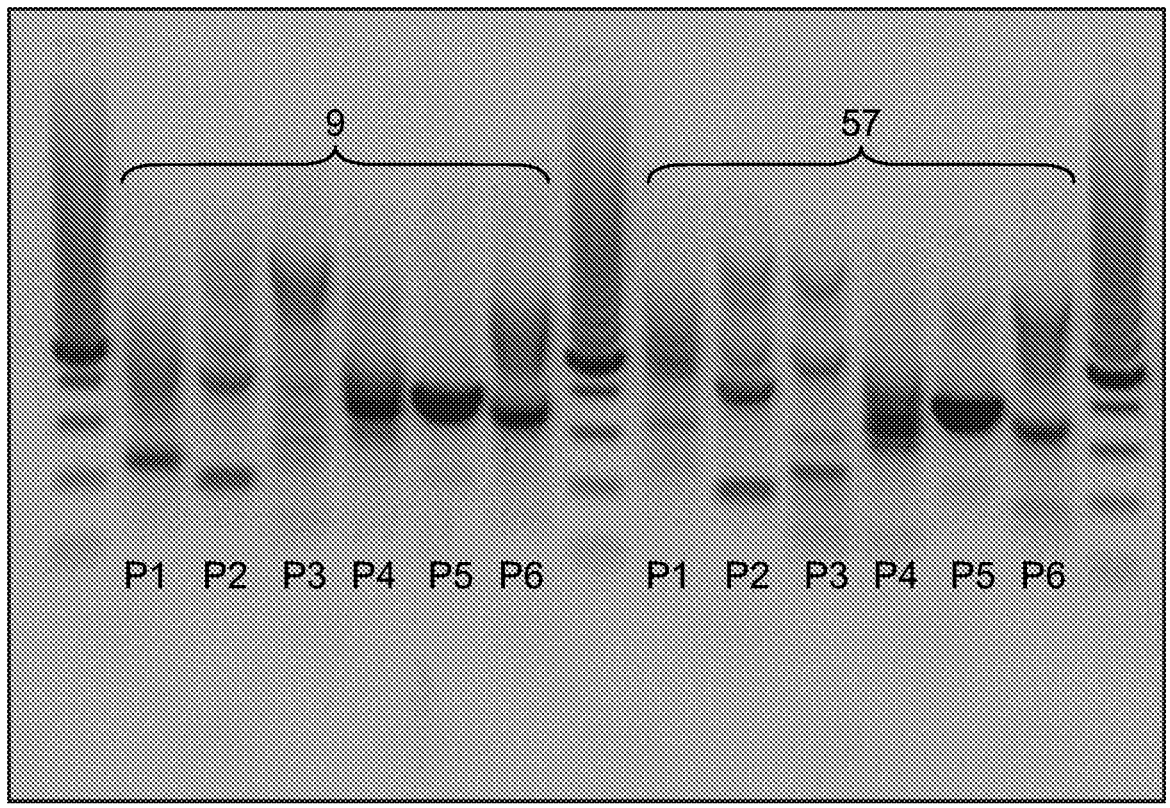
FIG. 11 is a photograph displaying RAPD PCR profiles for *Bacillus* strain 9 (NRRL No. B-67709) and *Bacillus* strain 57 (NRRL No. B-67710).
Figure 12:
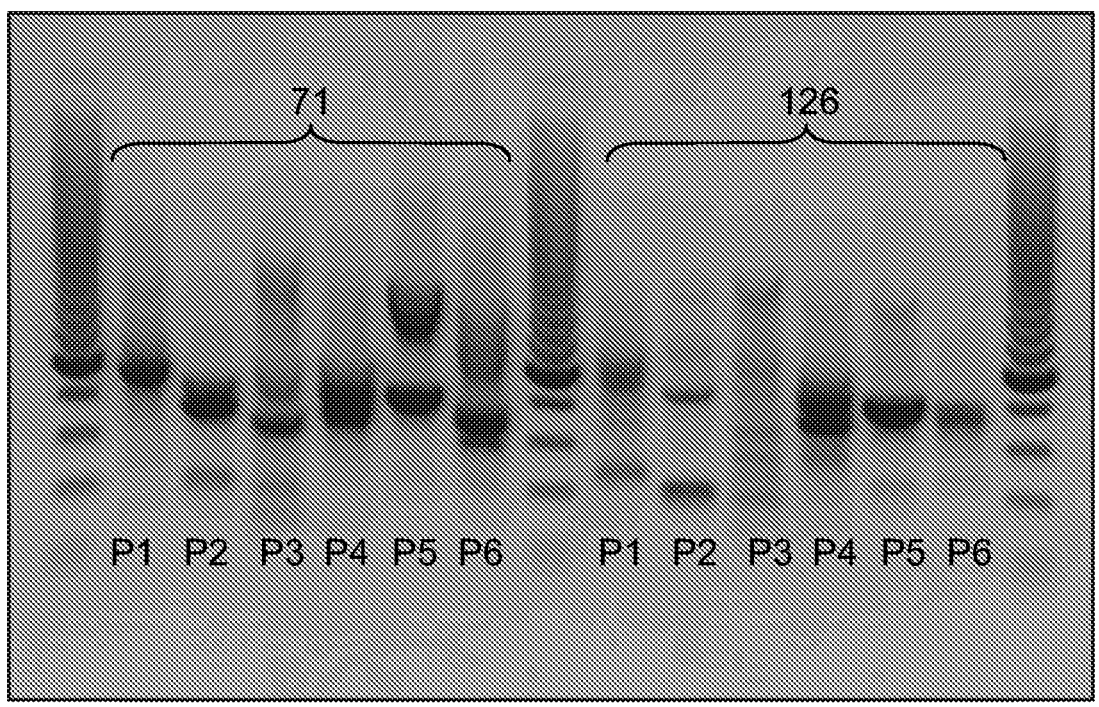
FIG. 12 is a photograph displaying RAPD PCR profiles for *Bacillus* strain 71 (NRRL No. B-67709) and *Bacillus* strain 126 (NRRL No. B-67710).

The Randomly Amplified Polymorphic DNA PCR method (hereafter referred to as RAPD-PCR) was used to identify genetic variability of each strain. Preparation of the DNA to be used in the RAPD-PCR reaction was done by using the QIAGEN® Tissue and Blood single column kit (QIAGEN®, Venlo, The Netherlands). FIGS. 7, 11, and 12 illustrate RAPD-PCR results for strains 2, 3, 4, 5, 6, 7, 9, 57, 71, and 126, with the unlabeled lanes or the lanes labeled "PC" being a molecular weight ladder. The results show that all strains are unique from each other.

What is claimed is:

1. A method of enhancing the efficacy of an antibiotic treatment and inhibit the growth of antibiotic resistant bacteria in an animal, the method comprising the step of
administering to the animal a feed composition or drinking water comprising an effective amount of an additive, wherein said additive comprises an isolated *Bacillus* strain selected from the group consisting of *Bacillus* strain 2 deposited as NRRL No. B-67709, *Bacillus* strain 3 deposited as NRRL No. B-67710, *Bacillus* strain 4 deposited as NRRL No. B-67711, *Bacillus* strain 5 deposited as NRRL No. B-67712, *Bacillus* strain 6 deposited as NRRL No. B-67714, *Bacillus* strain 7 deposited as NRRL No. B-67713, *Bacillus* strain 9 deposited as NRRL No. B-67866, *Bacillus* strain 57 deposited as NRRL No. B-67870, *Bacillus* strain 71 deposited as NRRL No. B-67867, *Bacillus* strain 126 deposited as NRRL No. B-67868, and combinations thereof, and
administering to the animal an antibiotic, wherein the administration of said additive in conjunction with said antibiotic enhances the efficacy of the antibiotic relative to administration of the antibiotic in the absence of the additive.

2. A method of enhancing the efficacy of an antibiotic treatment and inhibit the growth of antibiotic resistant bacteria in an animal, the method comprising the step of
administering to the animal a feed composition or drinking water comprising an effective amount of an additive, wherein said additive comprises an isolated *Bacillus* strain selected from the group consisting of *Bacillus* strain 2 deposited as NRRL No. B-67709, *Bacillus* strain 3 deposited as NRRL No. B-67710, *Bacillus* strain 4 deposited as NRRL No. B-67711, *Bacillus* strain 5 deposited as NRRL No. B-67712, *Bacillus* strain 6 deposited as NRRL No. B-67714, and *Bacillus* strain 7 deposited as NRRL No. B-67713, and combinations thereof, and
administering to the animal an antibiotic, wherein the administration of said additive in conjunction with said antibiotic enhances the efficacy of the antibiotic relative to administration of the antibiotic in the absence of the additive.

3. The method of claim 1 further comprising the step of administering to the animal another different bacterial strain selected from the group consisting of another *Bacillus* strain, a lactic acid bacterial strain, and combinations thereof.

4. The method of claim 2 wherein the strain administered is *Bacillus* strain 2 deposited as NRRL No. B-67709.

5. The method of claim 2 wherein the strain administered is *Bacillus* strain 3 deposited as NRRL No. B-67710.

6. The method of claim 2 wherein the strain administered is *Bacillus* strain 4 deposited as NRRL No. B-67711.

7. The method of claim 2 wherein the strain administered is *Bacillus* strain 5 deposited as NRRL No. B-67712.

8. The method of claim 2 wherein the strain administered is *Bacillus* strain 6 deposited as NRRL No. B-67714.

9. The method of claim 2 wherein the strain administered is *Bacillus* strain 7 deposited as NRRL No. B-67713.

10. The method of claim 1 wherein the *Bacillus* strain is administered in the feed composition at a dose of about $1.0 \times 10^3$ CFU/gram of the feed composition to about $5.0 \times 10^{12}$ CFU/gram of the feed composition.

11. The method of claim 1 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

12. The method of claim 1 wherein the animal is a sow and the *Bacillus* strain is administered during lactation.

13. The method of claim 1 wherein the animal is a sow and the *Bacillus* strain is administered during gestation.

14. The method of claim 1 wherein the feed composition is administered daily to the animal.

15. The method of claim 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

16. The method of claim 1 further comprising the step of administering an antibiotic wherein the antibiotic is selected from the group consisting of tylosin, tilmicosin, avilamycin, gentamycin, carbadox, tiamulin, and neomycin.

17. The method of claim 1 wherein the strain administered is *Bacillus* strain 9 deposited as NRRL No. B-67866.

18. The method of claim 1 wherein the strain administered is *Bacillus* strain 57 deposited as NRRL No. B-67870.

19. The method of claim 1 wherein the strain administered is *Bacillus* strain 71 deposited as NRRL No. B-67867.

20. The method of claim 1 wherein the strain administered is *Bacillus* strain 126 deposited as NRRL No. B-67868.

21. A commercial package comprising an isolated *Bacillus* strain selected from the group consisting of *Bacillus* strain 2 deposited as NRRL No. B-67709, *Bacillus* strain 3 deposited as NRRL No. B-67710, *Bacillus* strain 4 deposited as NRRL No. B-67711, *Bacillus* strain 5 deposited as NRRL No. B-67712, *Bacillus* strain 6 deposited as NRRL No. B-67714, *Bacillus* strain 7 deposited as NRRL No. B-67713, *Bacillus* strain 9 deposited as NRRL No. B-67866, *Bacillus* strain 57 deposited as NRRL No. B-67870, *Bacillus* strain 71 deposited as NRRL No. B-67867, *Bacillus* strain 126 deposited as NRRL No. B-67868, and combinations thereof.

22. The method of claim 1 wherein the animal is selected from the group consisting of a poultry species, a porcine species, a caprine species, a bovine species, an ovine species, an equine species, and a companion animal.

\* \* \* \* \*